United States Patent
Stickle et al.

(10) Patent No.: US 12,416,696 B2
(45) Date of Patent: Sep. 16, 2025

(54) MODULAR RADIO-FREQUENCY COIL ASSEMBLIES OF A MAGNETIC RESONANCE SYSTEM

(71) Applicant: GE PRECISION HEALTHCARE LLC, Wauwatosa, WI (US)

(72) Inventors: Thomas Stickle, Moreland Hills, OH (US); Taylan Dalveren, North Ridgeville, OH (US); David Louis Seamon Anderson, Reno, NV (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 149 days.

(21) Appl. No.: 18/166,820

(22) Filed: Feb. 9, 2023

(65) Prior Publication Data
US 2024/0272254 A1 Aug. 15, 2024

(51) Int. Cl.
*G01R 33/34* (2006.01)
*A61B 5/055* (2006.01)

(52) U.S. Cl.
CPC ........ *G01R 33/34084* (2013.01); *A61B 5/055* (2013.01)

(58) Field of Classification Search
CPC .......................... A61B 5/055; G01R 33/34084
See application file for complete search history.

(56) References Cited

U.S. PATENT DOCUMENTS

| | | | |
|---|---|---|---|
| 9,612,304 B2 | 4/2017 | Biber et al. | |
| 2008/0309341 A1* | 12/2008 | Dooms | G01R 33/36 324/318 |
| 2015/0112187 A1 | 4/2015 | Petropoulos et al. | |
| 2019/0277926 A1* | 9/2019 | Stormont | G01R 33/54 |
| 2020/0033429 A1* | 1/2020 | Darnell | G01R 33/3692 |
| 2020/0081082 A1* | 3/2020 | Kundner | G01R 33/3415 |

FOREIGN PATENT DOCUMENTS

WO WO-2022229895 A1 * 11/2022 ....... G01R 33/34007

OTHER PUBLICATIONS

IP.com, "Modular Coil," IP.com No. IPCOM00233818D, Dec. 23, 2013, 4 pgs.
Graessl et al., "Modular 32-Channel Transceiver Coil Array for Cardiac MRI at 7.0T," Magnetic Resonance in Medicine, 72: 276-290, 2014.
Yeh et al., "A Flexible and Modular Receiver Coil Array for Magnetic Resonance Imaging," IEEE Transactions on Medical Imaging, vol. 38, No. 3, Mar. 2019.

(Continued)

*Primary Examiner* — Gregory H Curran
(74) *Attorney, Agent, or Firm* — Armstrong Teasdale LLP

(57) ABSTRACT

A radio frequency (RF) coil assembly for a magnetic resonance (MR) system is provided. The RF coil assembly includes one or more modules. A module of the one or more modules includes one or more RF coils, each RF coil including a coil loop that includes a wire conductor, the wire conductor formed into the coil loop. Each RF coil also includes a coupling electronics portion coupled with the coil loop. The module further includes an outlet coupled with coupling electronics portions of the one or more RF coils. The RF coil assembly further includes a wiring harness including module interfacing cables each configured to be electrically coupled with the outlet.

19 Claims, 16 Drawing Sheets

(56) References Cited

OTHER PUBLICATIONS

Nohava et al., "Perspectives in Wireless Radio Frequency Coil Development for Magnetic Resonance Imaging," Frontiers in Physics, vol. 8, Article 11, Feb. 21, 2020, DOI: 10.3389/fphy.2020.00011.

Zangos et al., "MR-guided biopsies with a newly designed cordless coil in an open low-field system: Initial findings," Eur Radiol, 2006, 16: 2044-2050, DOI 10.1007/s00330-005-0069-1.

* cited by examiner

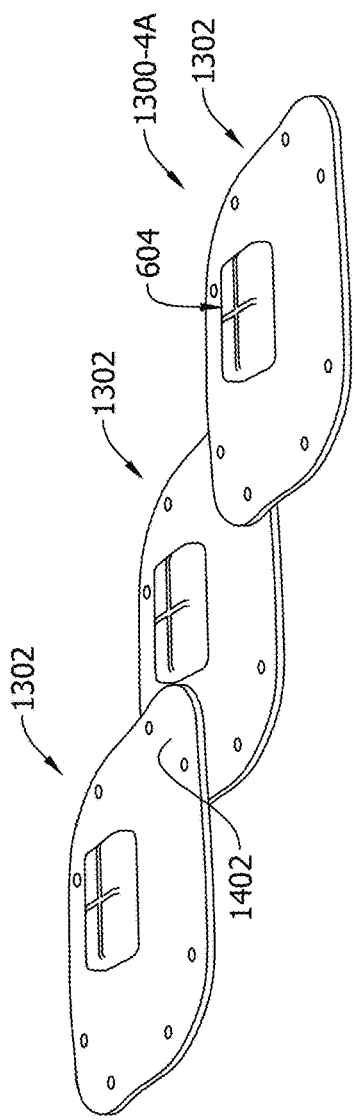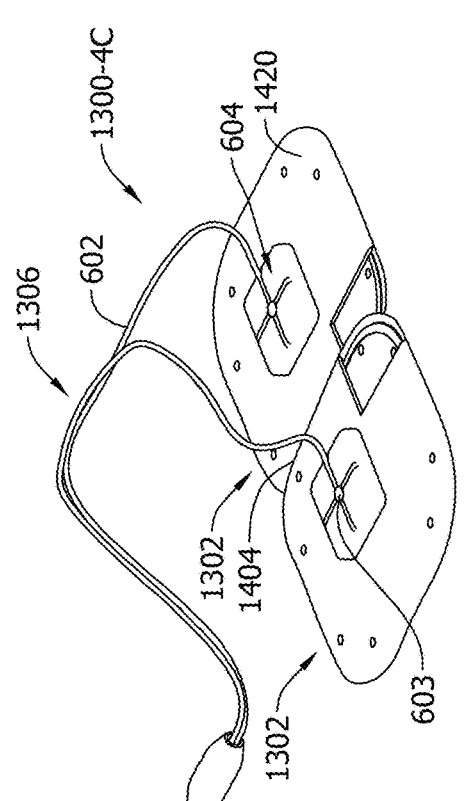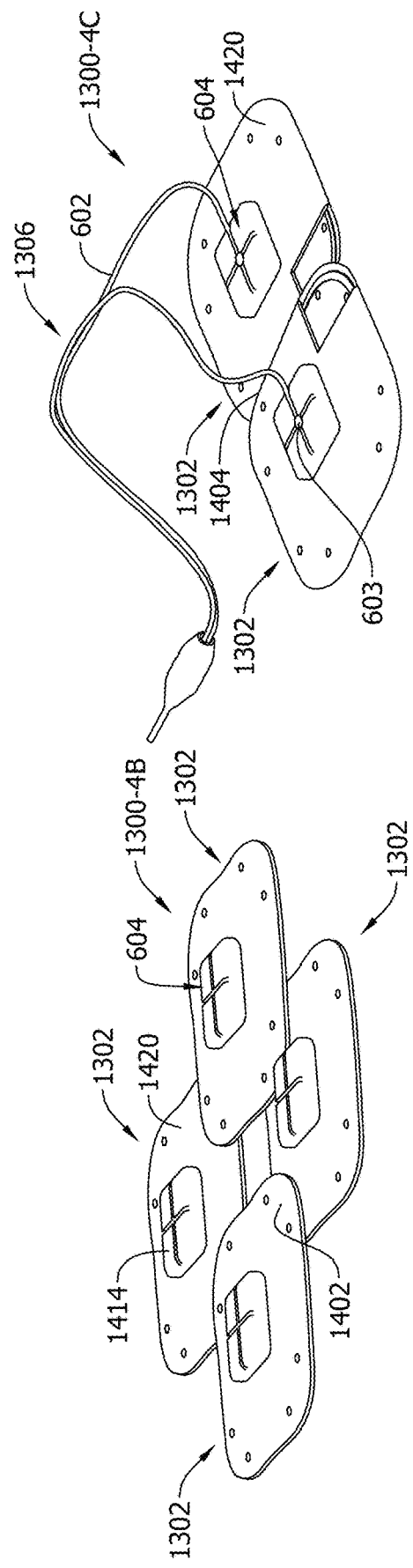

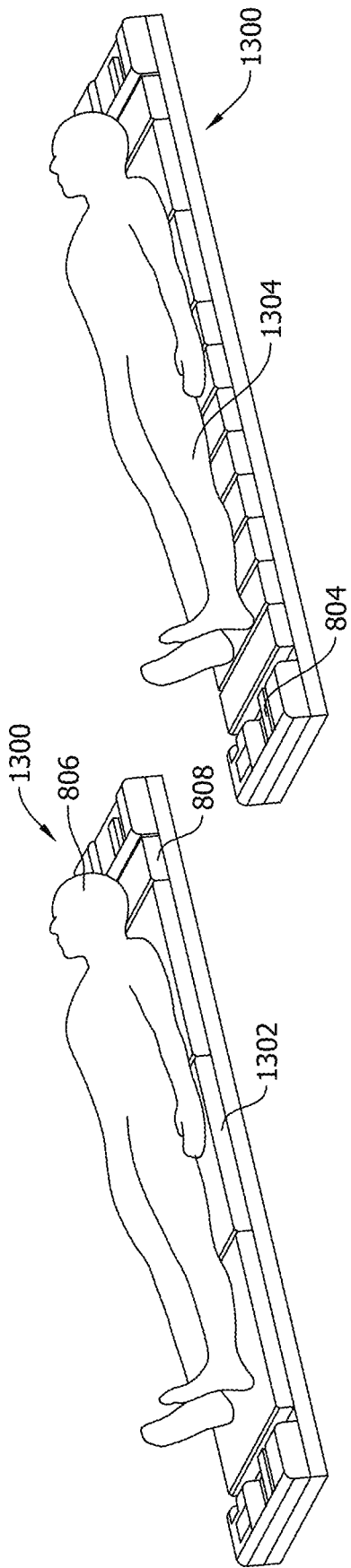
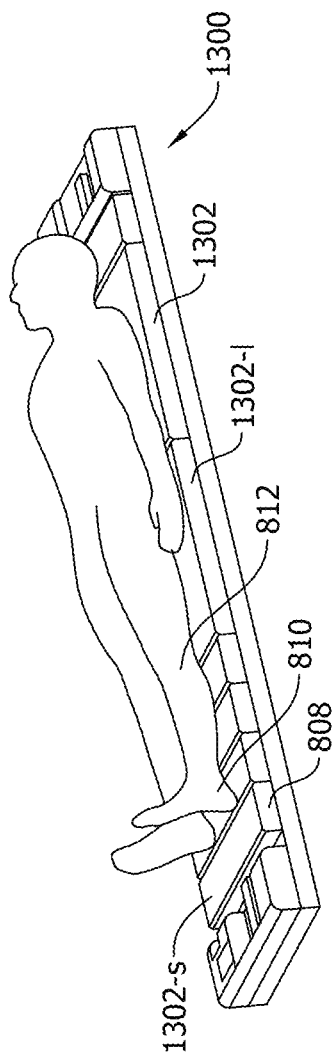
FIG. 8B
FIG. 8C
FIG. 8D

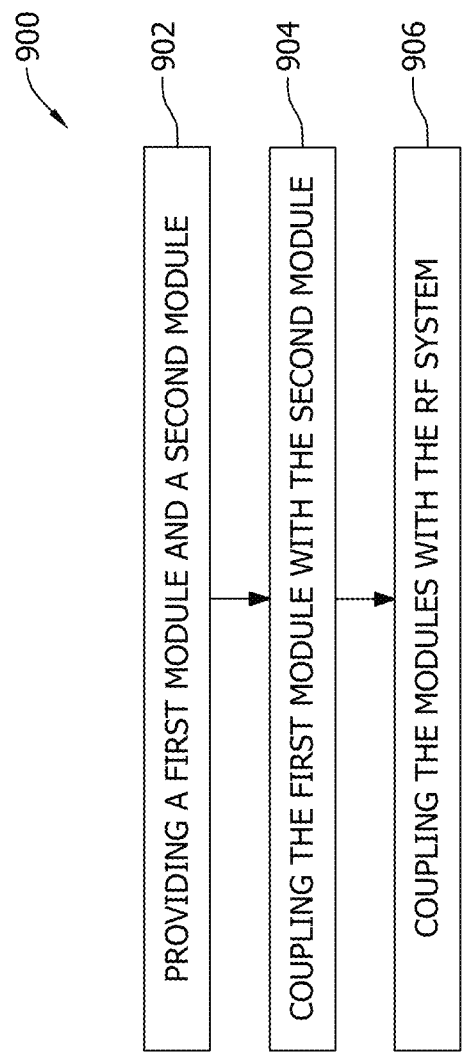

MODULAR RADIO-FREQUENCY COIL ASSEMBLIES OF A MAGNETIC RESONANCE SYSTEM

BACKGROUND

The field of the disclosure relates generally to a magnetic resonance (MR) system, and more particularly, to radio frequency (RF) coil assemblies for an MR system.

Magnetic resonance imaging (MRI) has proven useful in diagnosis of many diseases. MRI provides detailed images of soft tissues, abnormal tissues such as tumors, and other structures, which cannot be readily imaged by other imaging modalities, such as computed tomography (CT). Further, MRI operates without exposing patients to ionizing radiation experienced in modalities such as CT and x-rays.

In MRI, an RF coil assembly is used to detect MR signals emitted from a subject and thus is a key component of an MR system. Known RF coil assemblies are disadvantaged in some aspects and improvements are desired.

BRIEF DESCRIPTION

In one aspect, a radio frequency (RF) coil assembly for a magnetic resonance (MR) system is provided. The RF coil assembly includes one or more modules. A module of the one or more modules includes one or more RF coils, each RF coil including a coil loop that includes a wire conductor, the wire conductor formed into the coil loop. Each RF coil also includes a coupling electronics portion coupled with the coil loop. The module further includes an outlet coupled with coupling electronics portions of the one or more RF coils. The RF coil assembly further includes a wiring harness including module interfacing cables each configured to be electrically coupled with the outlet.

In another aspect, an RF coil assembly for an MR system is provided. The RF coil assembly includes a first module and a second module. The first module includes a first number of RF coils, each RF coil including a coil loop. The first module also includes a first outer enclosure housing coil loops of the first number of RF coils. The second module includes a second number of RF coils, the second number being different from the first number. The second module further includes a second outer enclosure housing coil loops of the second number of RF coils.

In one more aspect, a module of an RF coil assembly for an MR system is provided. The module includes one or more RF coils, each RF coil including a coil loop that includes a wire conductor, the wire conductor formed into the coil loop. Each RF coil also includes a coupling electronics portion coupled with the coil loop. The module further includes an outlet coupled with coupling electronics portions of the one or more RF coils.

BRIEF DESCRIPTION OF DRAWINGS

Non-limiting and non-exhaustive embodiments are described with reference to the following figures, wherein like reference numerals refer to like parts throughout the various drawings unless otherwise specified.

FIG. 4A shows another example RF coil assembly.
FIG. 4B shows one more example RF coil assembly.
FIG. 4C shows one more example RF coil assembly.
FIG. 8B shows one more example coil assembly.
FIG. 8C shows one more example coil assembly.
FIG. 8D shows one more example coil assembly.
FIG. 9 is a flow chart of an example method of assembling an RF coil assembly shown in FIGS. 1, 3A-6B, and 8A-8D.

DETAILED DESCRIPTION

The disclosure includes radio frequency (RF) coil assemblies for use in magnetic resonance (MR) systems for scanning a subject. As used herein, a subject is a human, an animal, a phantom, or any object scanned by a medical imaging system. MR imaging is described as an example only. The assemblies, systems, and methods described herein may be used for MR spectroscopy. MR systems are described as examples only. The RF coil assemblies and methods of assembling RF coil assemblies described herein may be used for medical imaging systems other than MR systems, such as positron emission tomography (PET)-MR systems. Method aspects of assembling and using the RF coil assemblies will be in part apparent and in part explicitly discussed in the following description.

In MR imaging (MRI), a subject is placed in a magnet. When the subject is in the magnetic field generated by the magnet, magnetic moments of nuclei, such as protons, attempt to align with the magnetic field but precess about the magnetic field in a random order at the nuclei's Larmor frequency. The magnetic field of the magnet is referred to as B0 and extends in the longitudinal or z direction. In acquiring an MR image, a magnetic field (referred to as an excitation field B1), which is in the x-y plane and near the Larmor frequency, is generated by an RF coil and may be used to rotate, or "tip," the net magnetic moment Mz of the nuclei from the z direction to the transverse or x-y plane. A signal, which is referred to as an MR signal, is emitted by the nuclei, after the excitation signal B1 is terminated. To use the MR signals to generate an image of a subject, magnetic field gradient pulses ($G_x$, $G_y$, and $G_z$) are used. The gradient pulses are used to scan through the k-space, the space of spatial frequencies or inverse of distances. A Fourier relationship exists between the acquired MR signals and an image of the subject, and therefore the image of the subject can be derived by reconstructing the MR signals.

Figure 1:
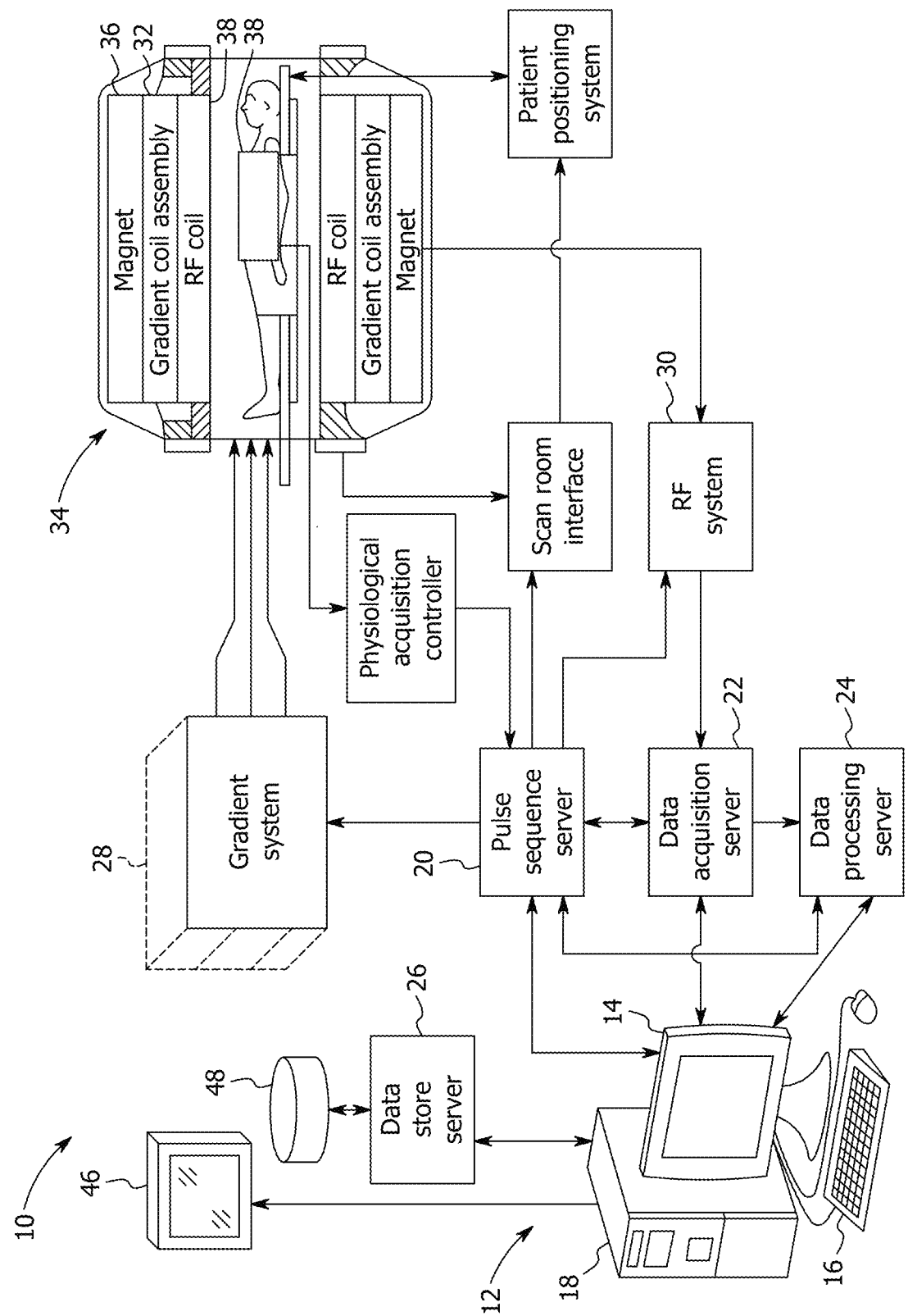
FIG. 1 is a block diagram of a magnetic resonance (MR) system.

FIG. 1 illustrates a schematic diagram of an example MR system 10. In the example embodiment, MR system 10 includes a workstation 12 having a display 14 and a keyboard 16. Workstation 12 includes a processor 18, such as a commercially available programmable machine running a commercially available operating system. Workstation 12 provides an operator interface that allows scan prescriptions to be entered into MR system 10. Workstation 12 is coupled to a pulse sequence server 20, a data acquisition server 22, a data processing server 24, and a data store server 26. Workstation 12 and each server 20, 22, 24, and 26 communicate with each other.

In the example embodiment, pulse sequence server 20 responds to instructions downloaded from workstation 12 to operate a gradient system 28 and an RF system 30. The instructions are used to produce gradient and RF waveforms in MR pulse sequences. An RF coil assembly 38 and a gradient RF coil assembly 32 are used to perform the prescribed MR pulse sequence. RF coil assembly 38 may be a whole body RF coil. RF coil assembly 38 may also be a local RF coil assembly 38 that may be placed in proximity to the anatomy to be imaged, or a coil array that includes a plurality of coils.

In the example embodiment, gradient waveforms used to perform the prescribed scan are produced and applied to gradient system 28, which excites gradient coils in gradient RF coil assembly 32 to produce the magnetic field gradients $G_x$, $G_y$, and $G_z$ used for position-encoding MR signals. Gradient RF coil assembly 32 forms part of a magnet assembly 34 that also includes a polarizing magnet 36 and RF coil assembly 38.

In the example embodiment, RF system 30 includes an RF transmitter for producing RF pulses used in MR pulse sequences. The RF transmitter is responsive to the scan prescription and direction from pulse sequence server 20 to produce RF pulses of a desired frequency, phase, and pulse amplitude waveform. The generated RF pulses may be applied to RF coil assembly 38 by RF system 30. Responsive MR signals detected by RF coil assembly 38 are received by RF system 30, amplified, demodulated, filtered, and digitized under direction of commands produced by pulse sequence server 20. RF coil assembly 38 is described as a transmit and receive coil such that RF coil assembly 38 transmits RF pulses and detects MR signals. In one embodiment, MR system 10 may include a transmit RF coil that transmits RF pulses and a separate receive coil that detects MR signals. A transmission channel of RF system 30 may be connected to an RF transmit coil and a receiver channel may be connected to a separate RF receive coil. Often, the transmission channel is connected to the whole body RF coil assembly 38 and each receiver section is connected to a separate local RF coil.

In the example embodiment, RF system 30 also includes one or more RF receiver channels. Each RF receiver channel includes an RF amplifier that amplifies the MR signal received by RF coil assembly 38 to which the channel is connected, and a detector that detects and digitizes the I and Q quadrature components of the received MR signal. The magnitude of the received MR signal may then be determined as the square root of the sum of the squares of the I and Q components as in Eq. (1) below:

$$M = \sqrt{I^2 + Q^2};\qquad(1)$$

and the phase of the received MR signal may also be determined as in Eq. (2) below:

$$\varphi = \tan^{-1}\left(\frac{Q}{I}\right).\qquad(2)$$

In the example embodiment, the digitized MR signal samples produced by RF system 30 are received by data acquisition server 22. Data acquisition server 22 may operate in response to instructions downloaded from workstation 12 to receive real-time MR data and provide buffer storage such that no data is lost by data overrun. In some scans, data acquisition server 22 does little more than pass the acquired MR data to data processing server 24. In scans that need information derived from acquired MR data to control further performance of the scan, however, data acquisition server 22 is programmed to produce the needed information and convey it to pulse sequence server 20. For example, during prescans, MR data is acquired and used to calibrate the pulse sequence performed by pulse sequence server 20. Also, navigator signals may be acquired during a scan and used to adjust the operating parameters of RF system 30 or gradient system 28, or to control the view order in which k-space is sampled.

In the example embodiment, data processing server 24 receives MR data from data acquisition server 22 and processes it in accordance with instructions downloaded from workstation 12. Such processing may include, for example, Fourier transformation of raw k-space MR data to produce two or three-dimensional images, the application of filters to a reconstructed image, the performance of a back-projection image reconstruction of acquired MR data, the generation of functional MR images, and the calculation of motion or flow images.

In the example embodiment, images reconstructed by data processing server 24 are conveyed back to, and stored at, workstation 12. In some embodiments, real-time images are stored in a database memory cache (not shown in FIG. 1), from which they may be output to operator display 14 or a display 46 that is located near magnet assembly 34 for use by attending physicians. Batch mode images or selected real time images may be stored in a host database on disc storage 48 or on a cloud. When such images have been reconstructed and transferred to storage, data processing server 24 notifies data store server 26. Workstation 12 may be used by an operator to archive the images, produce films, or send the images via a network to other facilities.

During a scan, interfacing cables may be used to transmit signals between RF coil assembly 38 and other aspects of MR system 10 (e.g., RF system 30, data acquisition server 22, and pulse sequence server 20), for example to control the RF coils and/or to receive signals from the RF coils. As described above, the RF coil assembly 38 may be a transmit coil that transmits RF excitation signals, or a receive coil that receives the MR signals emitted by the subject. In an example, the transmit and receive coils are a single mechanical and electrical structure or array of structures, with transmit/receive mode switchable by auxiliary circuitry. In other examples, a transmit coil and a receive coil may be independent structures that are physically coupled to each other via the RF system 30. For enhanced image quality, however, a receive coil is desirable to be mechanically and electrically isolated from the transmit coil. In such cases, the receive coil in the receive mode is electromagnetically coupled to and resonant with an RF "echo" that is stimulated by the transmit coil. On the other hand, during a transmit mode, the receive coil is electromagnetically decoupled from and therefore not resonant with the transmit coil, during transmission of the RF signal. Such decoupling averts a potential problem of noise produced within the auxiliary circuitry when the receive coil couples to the full power of the RF signal.

A traditional receive coil for MR includes several conductive intervals joined between themselves by capacitors. By adjusting the capacitors' values, the impedance of the RF coil may be brought to its minimal value, usually characterized by a low resistance. At a resonant frequency, stored magnetic and electric energy alternate periodically. Each conductive interval, due to its length and width, possesses a certain self-capacitance, where electric energy is periodically stored as static electricity. The distribution of this electricity takes place over the entire conductive interval length in the order of 5-15 cm, causing similar range electric dipole field. In proximity of a large dielectric load, self-capacitance of the intervals change, resulting in detuning of the coil. In case of a lossy dielectric, dipole electric field causes Joule dissipation characterized by an increased overall resistance observed by the coil.

Traditional RF coils may include acid etched copper traces or loops on printed circuit boards (PCBs) with lumped electronic components (e.g., capacitors, inductors, baluns, and resisters), matching circuitry, decoupling circuitry, and pre-amplifiers (see FIGS. 2A-2D described later). Such a configuration is typically bulky, heavy, and rigid, and requires relatively strict placement of the coils relative to each other in an array to prevent coupling interactions among coil elements that may degrade image quality. As such, traditional RF coils and RF coil arrays lack flexibility and therefore may not conform to subject anatomy, degrading imaging quality and subject comfort.

Figure 2B:
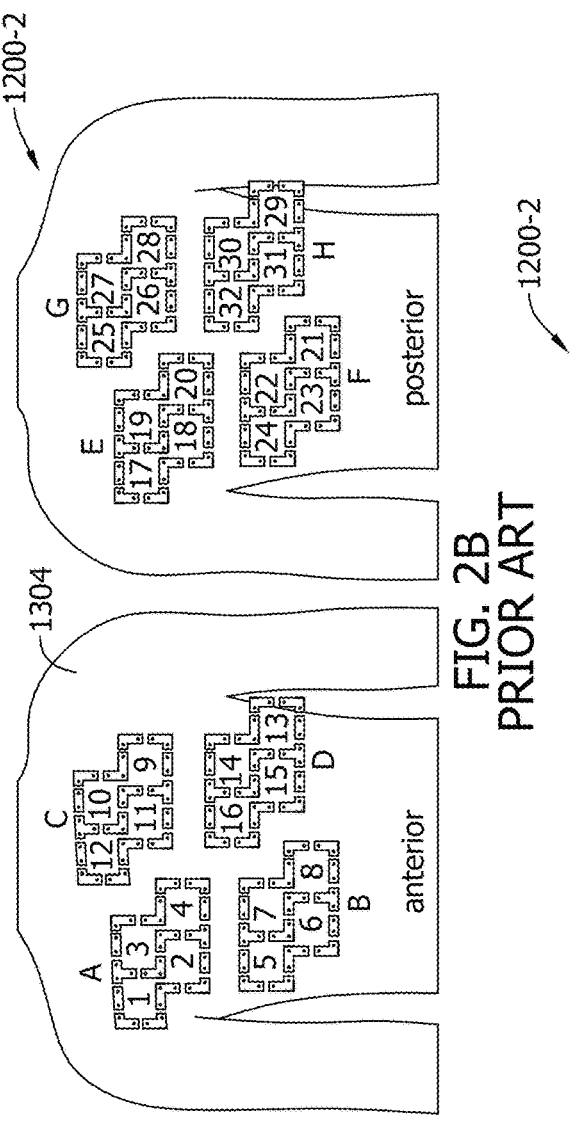
FIG. 2B is a schematic diagram of placement of coils of the known RF coil assembly shown in FIG. 2A.
Figure 2A:
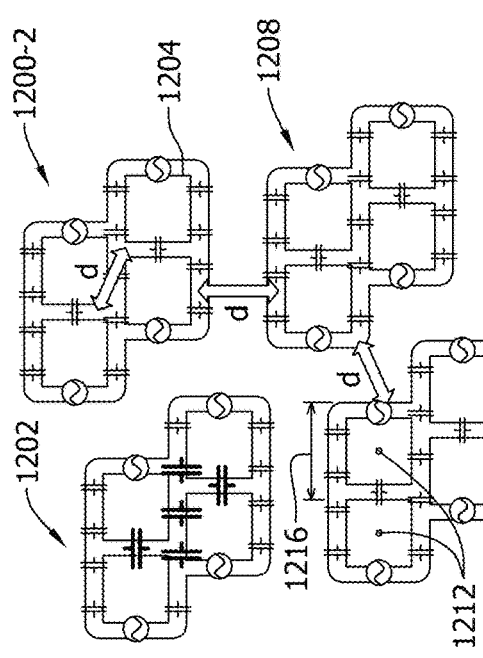
FIG. 2A is a schematic diagram of electronic components of a known radio frequency (RF) coil assembly.
Figure 2D:
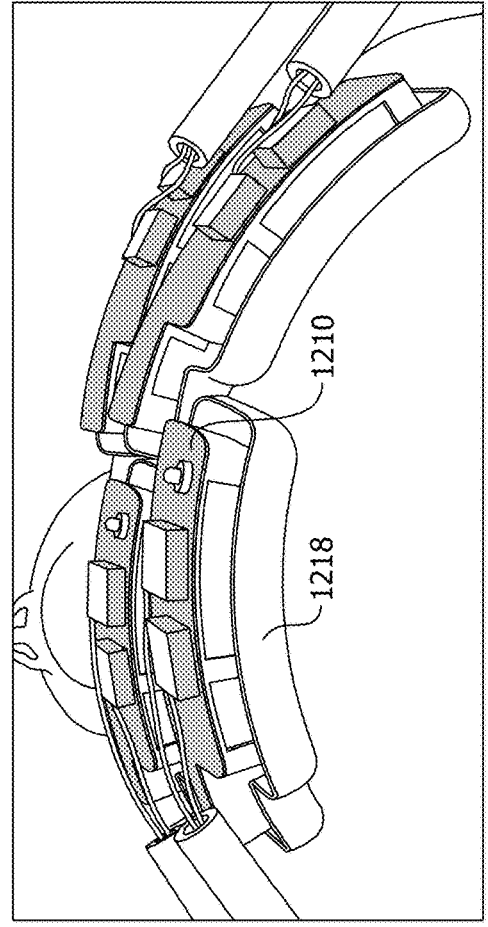
FIG. 2D illustrates the known RF coil assembly shown in FIG. 2A being placed on a subject with top covers of the RF coil assembly removed.
Figure 2C:
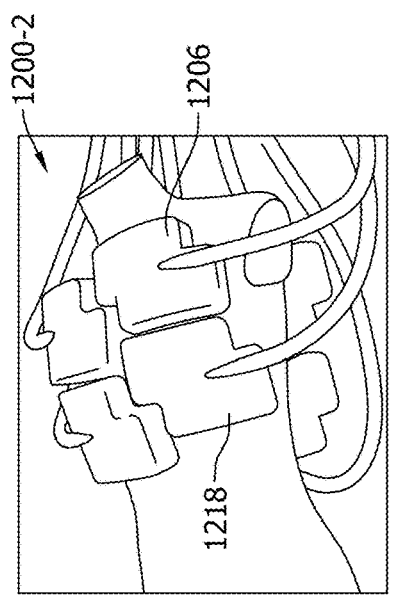
FIG. 2C illustrates the known RF coil assembly shown in FIG. 2A being placed on a subject.

FIGS. 2A-2D show a known RF coil assembly 1200 including modules 1202 constructed with traditional RF coils and RF coil arrays. FIG. 2A is a schematic diagram of the circuit elements of RF coil assembly 1200. FIG. 2B shows placement of modules on a subject 1304. FIG. 2C shows RF coil assembly 1200 being placed with subject 1304. FIG. 2D shows a top portion of RF coil assembly 1200 placed on subject 1304 with top covers 1206 of modules 1202 removed. RF coil assembly 1200 includes eight modules 1202, four modules 1202 to be placed over subject 1304. and four modules 1202 to be placed underneath subject 1304. In each module 1202, four coils 1208 are included. An individual coil 1208 includes a copper strip or copper trace 1210, which is rigid and heavy.

Two coil loops can couple magnetically and electrically. One form of coupling is mutual inductance where signals and noise are transferred from one coil loop to another. Coupling of coil loops introduces artifacts and reduces signal to noise ratio (SNR). The mutual inductance may be reduced by overlapping the coil loops or placing the coil loops at a distance. Coil X is overlapped with coil Y when the area defined by a coil loop of coil X overlaps or intersects with the area defined by a coil loop of coil Y. For example, in module A, coil 1 is overlapped with coils 2 and 3 (see FIGS. 2A and 2B). For traditional coil loops, critical overlapping is needed to minimize coupling between adjacent coil when using overlapping to reduce coupling. Two coil loops are critically overlapped when the mutual inductance coupling between the two coil loops is zero or approximately zero. For square coil loops 1204, if centers 1212 of square coil loops 1204 are separated by approximately 0.9 of length 1216 of an edge of square coil loop 1204. Coil loops 1204 are overlapped with one another to reduce mutual inductance coupling. Modules 1202 are underlapped from one another. A coil is underlapped from another coil when the coil is not overlapped with the other coil at any part of the coil. Module X is underlapped with module Y when any coil of module X is underlapped with any coil of module Y. For example, module A is underlapped with modules B, C., or D (see FIGS. 2A and 2B). A minimum distance is required to minimize the coupling between two loops. The minimum distance depends on the coil construction and the tolerance level for coupling. However, when the two coil loops are too far apart, signals of anatomies at the gap between the two coil loops are not received in either coil loop, causing a gap in the image.

Because of the rigid requirement on coil distance and construction, modules 1202 in known RF coil assembly 1200 need to be fitted in a predefined manner like puzzle pieces. If modules 1202 are not assembled in the predefined manner, image quality is compromised. Therefore, nonfunctioning of one module 1202 renders the entire RF coil assembly 1200 nonfunctioning, resulting in decommission of the entire RF coil assembly 1200.

Further, because the rigid requirement on coil distance and construction, rigid structure is needed to keep the formation of the coil. As shown in FIG. 2D, coil loops 1204 are fabricated from copper strips 1210. Copper strips 1210 are fastened to an enclosure 1218 of module 1202. Enclosures 1218 are also rigid to keep the placement and shape of copper strips 1210.

In contrast, the RF coil used in the RF coil assemblies described herein includes a coil loop formed by wire conductors. In the case of two RF coils overlapping, the coupling electronics portion that couples with the coil loop of the RF coil has high blocking or source impedance, thereby minimizing mutual inductance coupling. A thin cross-section of the wire conductor in the RF coil reduces the parasitic capacitance at the cross-overs or overlaps, and reduces other coupling such as electric field coupling and eddy current, in comparison to two traditional trace-based loops. The combination of high blocking impedance and a thin cross-section of the RF coil loop allows flexible placement of multiple coils into one RF coil assembly over a finite area, while coupling between the RF coils is minimized and critical overlapping between two loops is not required. Wire conductors also add flexibility to the coils, allowing the RF coil assembly to conform with a curved anatomy of a subject.

Figure 3B:
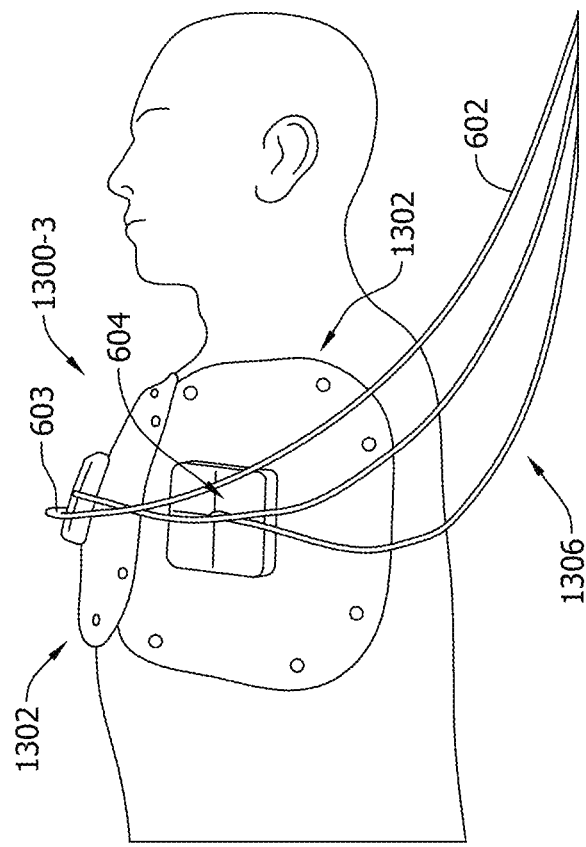
FIG. 3B is a side view of the RF coil assembly shown in FIG. 3A.
Figure 3A:
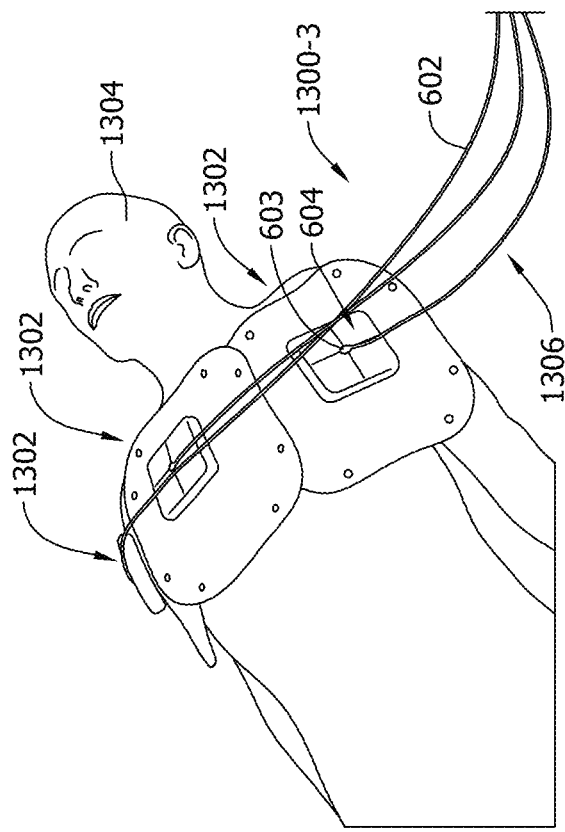
FIG. 3A is a perspective view of an example RF coil assembly placed on a subject.

FIGS. 3A and 3B show an example RF coil assembly 1300-3 including modules 1302 that are pluggable and serviceable. FIG. 3A is a perspective view of RF coil assembly 1300 placed on subject 1304. FIG. 3B is a side view of RF coil assembly 1300 placed on subject 1304. In the example embodiment, RF coil assembly 1300 may further include wiring harness 1306. Modules 1302 are coupled with wiring harness 1306. The other end of wiring harness 1306 is coupled with one of system ports of MR system 10. The number of ports in MR system 10 is limited. MR system 10 typically includes four ports, each providing a certain number of channels such as 16, 32, or 64 channels, or other numbers of channels. Signals from and to RF coils 202 are transmitted via ports to RF system 30.

FIGS. 4A-4E show more example RF coil assemblies 1300-4A, 1302-4B, 1302-4C, 1302-4D, and 1302-4E. In the example embodiments, modules 1302 of RF coil assembly 1300 are coupled with one another at arbitrary orientations. A module 1302 of RF coil assembly 1300-4A, 1302-4B is coupled with another module 1302 at corners 1402 of modules 1302. A module 1302 of RF coil assembly 1300-4C is coupled with another module along edges 1404 of modules 1302. Module 1302 is shown as in a square or rectangular shape. Modules 1302 may in other shapes such as circular and polygonal or in irregular shapes. Modules 1302 may be in the same shapes or sizes such that spare modules 1302 may be provided in a scanner room and used to replace a nonfunctioning module 1302 of RF coil assembly 1300. Modules 1302 may be in different shapes or sizes and spare modules 1302 of corresponding shapes or sizes may be provided for replacement.

In the example embodiments, modules 1302 are not restricted at a predefined distance with one another. A module 1302 may be overlapped with another module 1302 in RF coil assembly 1300-3, 1302-4A, 1302-4B, and 1302-4C. Module X is overlapped with module Y when a coil of module X is overlapped with a coil of module Y. RF coil assembly 1300 may further include mechanical features such as couplers 1408 (see FIG. 4D) on modules 1302 that allow modules 1302 to be connected to one another to maintain the overlap distance between modules 1302 or keep modules 1302 in place during the use of RF coil assembly 1300.

In the example embodiments, RF coil assembly 1300-4D, 1302-4E may include modules 1302 that are underlapped. Underlapped modules 1302 may be in the S/I (superior/inferior) direction (see FIG. 4D) or in the R/L (right/left) direction (see FIG. 4E). For example, module 1302-4D1 is underlapped with module 1302-4D2. Coil loops 201 in module 1302-4D1 are underlapped with coil loops 201 in module 1302-4D2. The gap 1416 between neighboring coil loops 201 of underlapped modules 1302 may be 1 cm with a diameter 1410 of coil loop 201 as 13.6 cm. Modules 1302 of RF coil assembly 1300-4D, 1302-4E may be overlapped in the other direction. For example, modules 1302 in the S/I direction are underlapped, while modules 1302 are overlapped in the R/L direction in RF coil assembly 1300-4D. In RF coil assembly 1300-4E, modules 1302 are underlapped in the R/L direction while modules 1302 are overlapped in the S/I direction. In some embodiments, all modules 1302 in RF coil assembly are underlapped.

Figure 4D:
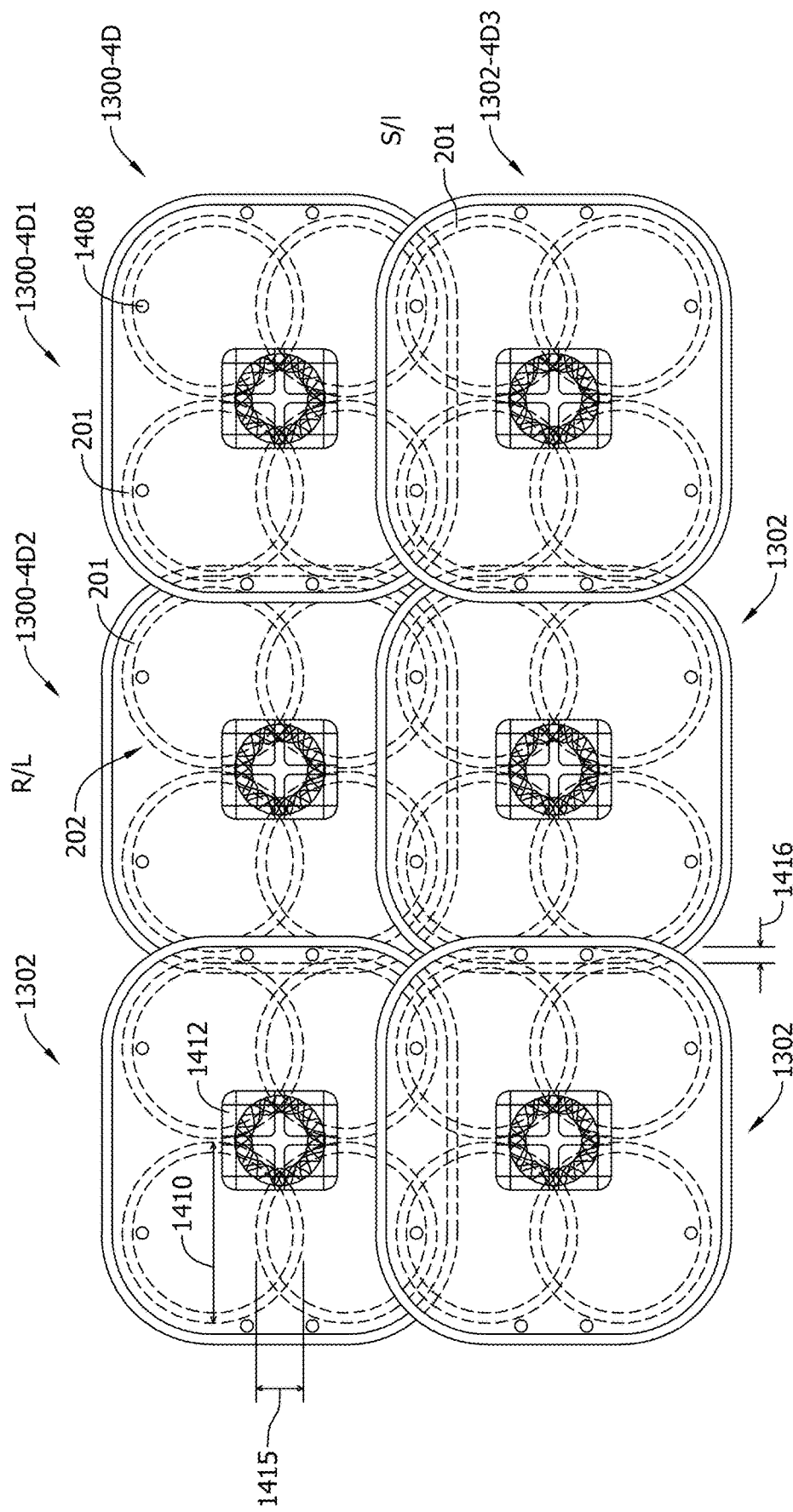
FIG. 4D shows one more example RF coil assembly.
Figure 4E:
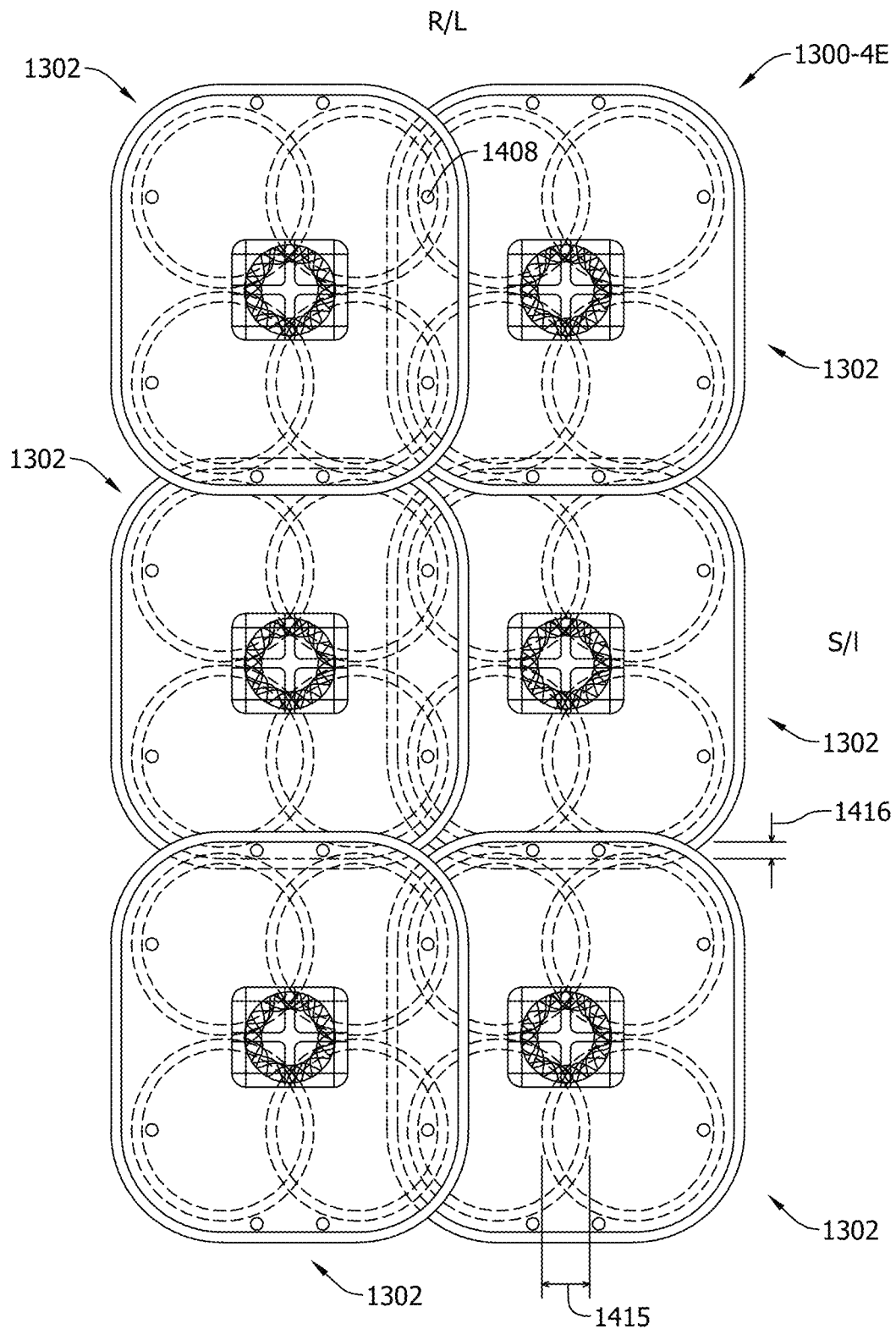
FIG. 4E shows one more example RF coil assembly.

In the example embodiments, module 1302 may include coupler 1408 (see FIG. 4D). Coupler 1408 is configured to couple modules 1302 together. For example, coupler 1408 may be a hook-and-loop fastener. Coupler 1408 also serves as a marker indicating positions at which module 1302 critically overlaps with another module 1302. When a coupler 1408 of module 1302 is aligned with a coupler 1408 of another module 1302, the two modules 1302 are critically overlapped, where the coils along the borders of modules 1302 are critically overlapped with one another. For circular coil loops, when one RF coil loop 201 overlaps with another RF coil loop 201 by approximately 25%, where the overlapped distance 1415 between the two RF coil loops is approximately 25% of the diameter 1410 of the RF coil loop 201, the two RF coil loops 201 are critically overlapped, where the mutual inductance coupling is zero or approximately zero. For circular coil loops 201 having diameters 1410 of 136 cm, an overlapped distance 1415 of 36 cm of coil loops 201 provides coil loops 201 with critical overlapping, where the coupling is minimized. Other orientations provide critical overlapping because coil loops are circular.

In the example embodiments, module 1302 includes one or more RF coils 202 (see FIG. 4D and FIGS. 5A-5D described later). RF coil 202 includes a coil loop 201 and a coupling electronics portion 203. Coupling electronics portion 203 or part of coupling electronics portion 203 of RF coils 202 in a module 1302 may be combined into one coupling electronics unit 1412 (see FIGS. 4D and 4E). Coupling electronics unit 1412 includes an electronics box 1414 housing coupling electronics portions 203 or part of coupling electronics portions 203 (see FIG. 4B). The electronic components of coupling electronics unit 1412 may be formed as one PCB. Alternatively, the electronic components may be formed on multiple PCBs. Coupling electronics unit 1412 further includes an outlet 604 sized to be coupled with wiring harness 1306 such that an module interfacing cable 602 of wiring harness is pluggable with outlet 604 (see FIGS. 3A-4C and FIGS. 6A and 6B described later). Outlet 604 may be a male or female outlet, and complementary to module interfacing cable 602 of wiring harness 1306. As a result, module 1302 is coupled with wiring harness 1306 by plugging module interfacing cable 602 with outlet 604 of module 1302, greatly increasing assembling convenience.

In the example embodiments, module 1302 includes an outer enclosure 1420 (see FIGS. 4B and 4C). Outer enclosure 1420 may be fabricated from a polyurethane fabric such as DARTEX®. The material for outer enclosure 1420 may be waterproof, semi-vapor permeable, and anti-fungal treated. The material allows for ease of cleaning, and protects the internal electronics from getting wet or soiled. Further, the material is biocompatible and does not irritate the skin of a human subject, and therefore suitable for medical uses. The material is also lighted weighted and flexible. Underneath outer enclosure 1420, module 1302 may include an inner enclosure (not shown). The inner enclosure covers RF coils 202. The inner enclosure may be fabricated from a material that provides padding, spacing, and/or flame-retardant properties, such as NOMEX®. Outer enclosure 1420 may further include fasteners, for example hook-and-loop fasters or adhesive patches, to hold modules in place after modules are coupled with one another.

In the example embodiments, coupling electronics unit 1412 is positioned exterior of outer enclosure 1420. Alternatively, coupling electronics unit 1412 is positioned inside outer enclosure 1420, with outlet 604 of coupling electronics unit 1412 extending through outer enclosure 1420 and being exposed to provide connection with wiring harness 1306.

In operation, to assembly RF coil assembly, modules 1302 are placed adjacent to one another at a desired orientation to cover a desired area of subject 1304. Module interfacing cables 602 of wiring harness 1306 are coupled with outlets 604 of modules 1302. Coil assembly interfacing connector 608 of wiring harness 1306 is plugged in a port of MR system.

In some embodiments, module 1302 includes a wireless communication unit 1424 configured to communicate with RF system 30 and/or other components of MR system 10 in a wireless mode (see FIG. 6B described later). Module 1302 wirelessly transmits and receives signals to and from RF system 30 and/or other components. Module 1302 may be powered by a battery assembly.

Figure 5A:
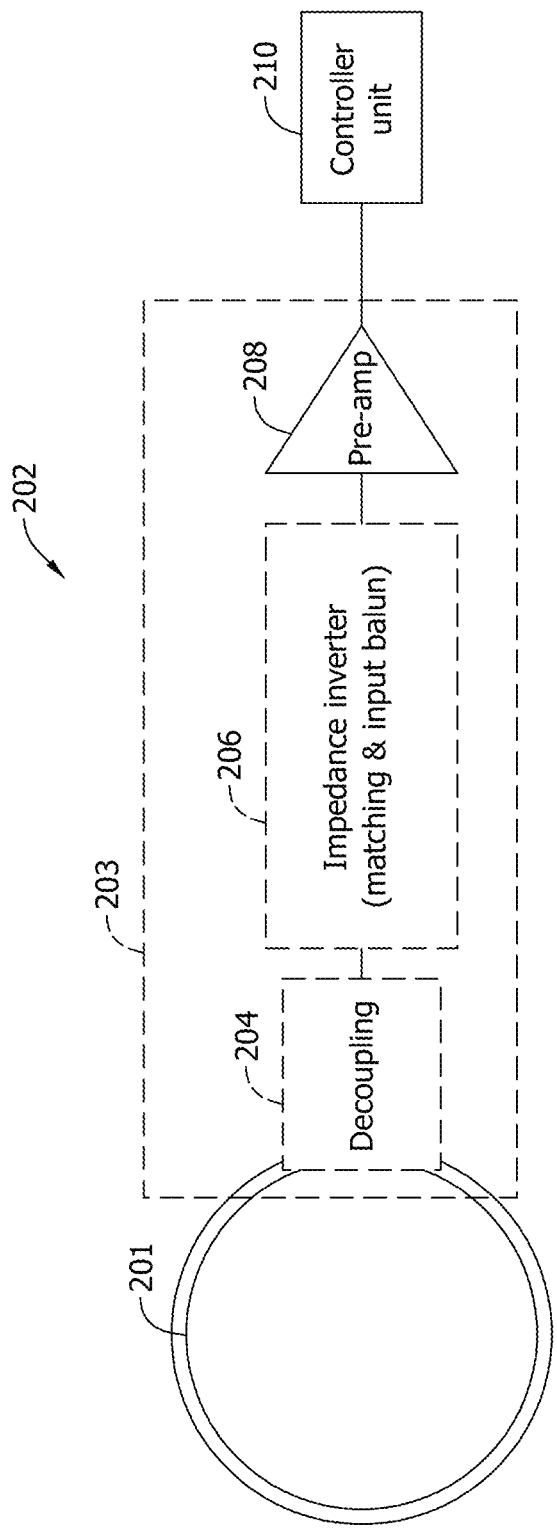
FIG. 5A is a block diagram of an example RF coil.
Figure 5B:
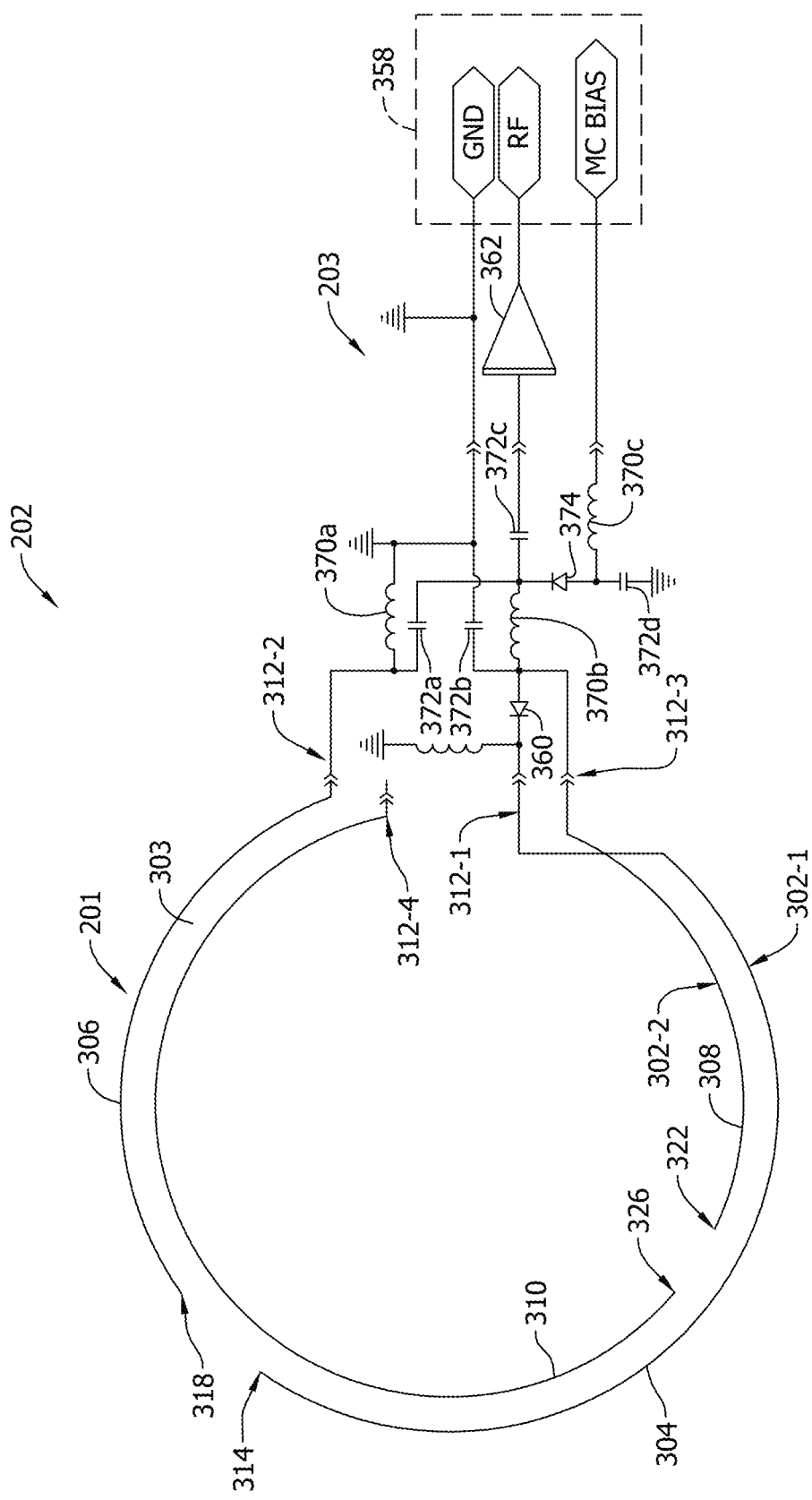
FIG. 5B is a schematic diagram of an example embodiment of the RF coil shown in FIG. 5A.
Figures 5C, 5D:
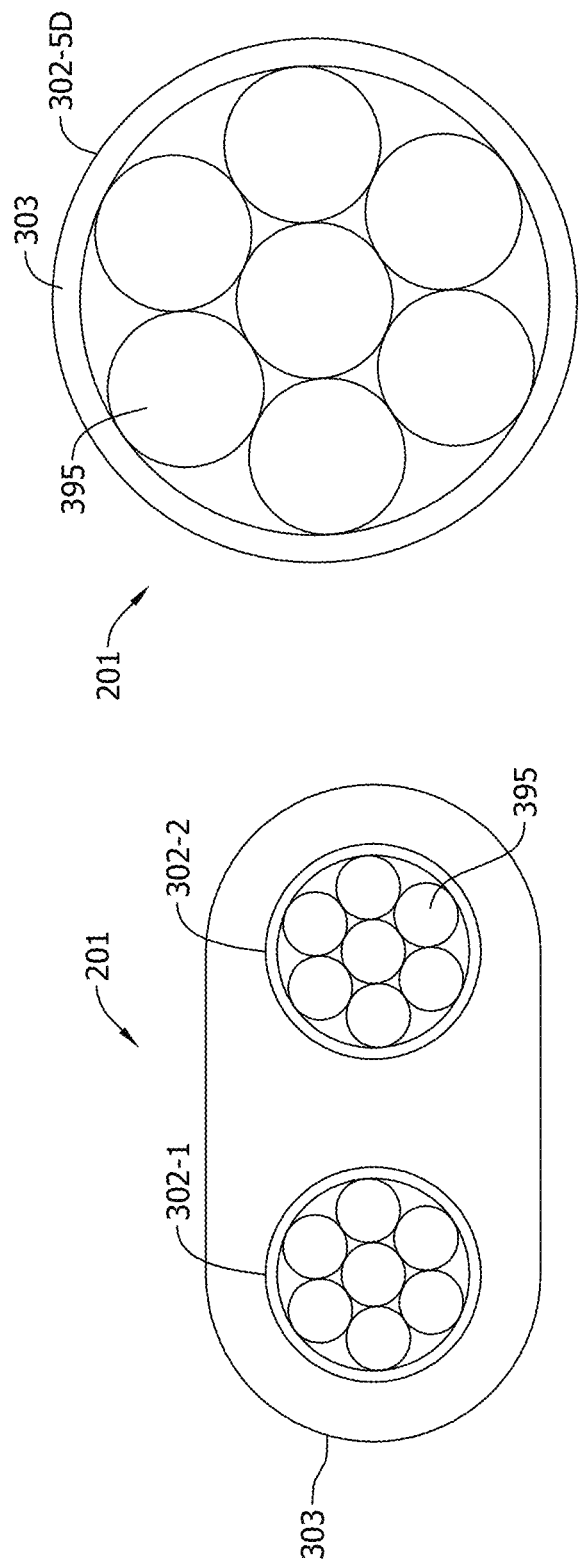
FIG. 5C is a cross-sectional view of an example coil loop of the RF coil shown in FIG. 5A.
FIG. 5D is a cross-sectional view of another example coil loop of the RF coil shown in FIG. 5A.

FIGS. 5A-5D show example RF coils 202 of module 1302. FIG. 5A is a block diagram of RF coil 202. FIG. 5B is a schematic diagram of RF coil 202. FIG. 5C is a cross-sectional view of example coil loop 201 of RF coil 202. FIG. 5D is a cross-sectional view of another example coil loop 201 of RF coil 202.

In the example embodiment, RF coil 202 includes coil loop 201 coupled to a controller unit 210 via a coupling electronics portion 203 and a coil-interfacing cable 212. In one example, the RF coil may be a surface receive coil, which may be single- or multi-channeled. RF coil 202 may operate at one or more frequencies in MR system 10. Coil-interfacing cable 212 may be a coil-interfacing cable extending between coupling electronics portion 203 or an module interfacing cable 602 extending between module 1302 and other components of MR system 10 such as RF system 30 (see FIGS. 6A and 6B described later).

As described above, one form of coupling is mutual inductance where signals and noise are transferred from one coil loop to another. The mutual inductance may be reduced by overlapping the coil loops. The mutual inductance may also be reduced by using a high blocking impedance in the coupling electronics portion. The blocking impedance $R_{block}$ seen by the coil loop in general depends on the resistance R of the coil loop, matching characteristic impedance $Z_0$ of the transmission line, and input impedance of the LNA (a linear amplifier or preamplifier) $R_{lna}$ and may be approximated as:

$$R_{block} = \frac{Z_0 R}{R_{lna}}.$$

When a relatively-high blocking impedance $R_{block}$ is used, $$\frac{X_L}{R} \le \frac{Z_0}{R_{lna}}$$

and the induced current from one coil loop to another is minimized, where $X_L = \omega_0 L$ is the reactance of the coil loop at the resonance frequency of the coil loop.

Other coupling such as coupling through electric field and eddy current may be minimized by reducing the cross-section of the wire conductor in coil loop 201.

In the example embodiment, coupling electronics portion 203 may be coupled to coil loop 201 of RF coil 202. Coupling electronics portion 203 may include a decoupling circuit 204, impedance inverter circuit 206, and a pre-amplifier 208. Decoupling circuit 204 may effectively decouple the RF coil during a transmit operation. Typically, RF coil 202 in the receive mode may be positioned adjacent a body of a subject being imaged by MR system 10 in order to receive echoes of the RF signal transmitted during the transmit mode. If RF coil 202 is not used for transmission, RF coil 202 is decoupled from the RF transmit coil such as the RF body coil when the RF transmit coil is transmitting the RF signal. The decoupling of the receive coil from the transmit coil may be achieved using resonance circuits and PIN diodes, microelectromechanical systems (MEMS) switches, or another type of switching circuitry. The switching circuitry may activate detuning circuits operatively connected to RF coil 202.

In the example embodiment, the impedance inverter circuit 206 may form an impedance matching network between RF coil 202 and pre-amplifier 208. Impedance inverter circuit 206 is configured to transform a coil impedance of RF coil 202 into an optimal source of impedance for pre-amplifier 208. The impedance inverter circuit 206 may include an impedance matching network and an input balun. Pre-amplifier 208 receives MR signals from corresponding RF coil 202 and amplifies the received MR signals. In one example, the pre-amplifier may have a low input impedance that is configured to accommodate a relatively high blocking or source impedance. Additional details regarding the RF coil and associated coupling electronics portion will be explained in more detail below with respect to FIG. 5B. Coupling electronics portion 203 may be packaged in a small PCB with a surface area of approximately 2 $cm^2$ or smaller. The PCB may be protected with a conformal coating or an encapsulating resin.

Coil-interfacing cable 212, such as an module interfacing cable, may be used to transmit signals between the RF coils and other components of MR system 10. The module interfacing cables may be disposed within the bore or imaging space of MR system 10 and subjected to electromagnetic fields produced and used by MR system 10. In MR systems, coil-interfacing cables 212 may support transmitter-driven common-mode currents, which may in turn create field distortions and/or unpredictable heating of components. Typically, common-mode currents are blocked by using baluns. Baluns or common-mode traps provide high common-mode impedances, which in turn reduces the effect of transmitter-driven currents.

In the example embodiment, coil-interfacing cable 212 may include one or more baluns. In traditional coil-interfacing cables, baluns are positioned with a relatively high density, because high dissipation/voltages may develop if the balun density is too low or if baluns are positioned at an inappropriate location. However, the dense placement may adversely affect flexibility, cost, and performance. As such, the one or more baluns in the coil-interfacing cable may be continuous baluns to ensure no high currents or standing waves, independent of positioning. The continuous baluns may be distributed, flutter, and/or butterfly baluns.

FIG. 5B is a schematic diagram of an example RF coil 202 having segmented conductors formed in accordance with an embodiment. RF coil 202 is a non-limiting example of RF coil 202 shown in FIG. 5A and as such includes coil loop 201 and coupling electronics portion 203. In the example embodiment, the coupling electronics portion allows the RF coil to transmit and/or receive RF signals when driven by RF system 30 (shown in FIG. 1). In the illustrated embodiment, RF coil 202 includes a first conductor 302-1 and a second conductor 302-2. First and second conductors 302-1, 302-2 may be segmented such that the conductors form an open circuit (e.g., form a monopole). The segments of conductors 302-1, 302-2 may have different lengths. The length of first and second conductors 302-1, 302-2 may be varied to achieve a select distributed capacitance (DCAP), and accordingly, a select resonance frequency. DCAP, as used herein, represents a capacitance exhibited between conductors that grows evenly and uniformly along the length of the conductors and is void of discrete or lumped capacitive components and discrete or lumped inductive components.

In the example embodiment, first conductor 302-1 includes a first segment 304 and a second segment 306. First segment 304 includes a driven end 312-1 at an interface terminating to coupling electronics portion 203. First segment 304 also includes a floating end 314 that is detached from a reference ground, thereby maintaining a floating state. Second segment 306 includes a driven end 312-2 at the interface terminating to the coupling electronics portion and a floating end 318 that is detached from a reference ground.

In the example embodiment, second conductor 302 includes a first segment 308 and a second segment 310. First segment 308 includes a driven end 312-3 at the interface. First segment 308 also includes a floating end 322 that is detached from a reference ground, thereby maintaining a floating state. Second segment 310 includes a driven end 312-4 at the interface, and a floating end 326 that is detached from a reference ground. Driven end 312-4 may terminate at the interface such that end 312-4 is only coupled to the first conductor through the distributed capacitance. The capacitors shown around the loop between the conductors represent the capacitance between the wire conductors.

In the examples herein, the capacitance may grow in a uniform manner along the length of first and second conductors 302-1, 302-2. For example, first conductor 302-1 exhibits a distributed capacitance that grows based on the length of first and second segments 304, 306. Second conductor 302-2 exhibits a distributed capacitance that grows based on the length of first and second segments 308, 310. First segments 304, 308 may have a different length than second segments 306, 310. The relative difference in lengths between first segments 304, 308 and second segments 306, 310 may be used to produce an effective LC circuit having a resonance frequency at the desired center frequency. For example, by varying the length of first segments 304, 308 relative to the lengths of second segments 306, 310, an integrated distributed capacitance may be varied.

In the illustrated embodiment, the first and second wire conductors 302-1, 302-2 are shaped into a coil loop that terminates to an interface. The coil loop defines a conductive pathway along the first and second conductors. The first and second conductors are void of any discrete or lumped capacitive or inductive elements along an entire length of the conductive pathway. FIG. 5B shows first and second conductors 302-1, 302-2 are segmented as an example. The coil loop may include loops of varying gauge of stranded or solid conductor wire, loops of varying diameters with varying lengths of first and second conductors 302-1, 302-2, and/or loops of varying spacing between first and second conductors 302-1, 302-2. For example, each of the first and second conductors may have no cuts or gaps (no segmented conductors, not shown) or one or more cuts or gaps (segmented conductors, FIG. 5B) at various locations along the conductive pathway.

In the example embodiment, circular coil loop 201 is depicted as an example only. Coil loop 201 may in other shapes, such as oval, irregularly curved, or rectangular, that enable coil loop 201 to function as described herein. In one example, coil loop 201 is fabricated from a flexible 1.3 millimeter (mm) diameter conductor optimized for zero reactance at 127.73 MHZ, the resonance frequency of a 3 T MR system. RF coils 202 may be designed for an MR system 10 having a different field strength, such as 1.5 T. Because wire conductor 302 of coil loop 201 is flexible, the shape of coil loop 201 may change and be deformed to conform to a curved anatomy of the subject, such as deforming from being circular to other shapes such as oval, elliptical, or irregular shapes like Pringles® chips.

In the example embodiment, a dielectric material 303 encapsulates and separates first and second conductors 302-1, 302-2. Dielectric material 303 may be selectively chosen to achieve a select distributive capacitance. Dielectric material 303 may be based on a desired permittivity e to vary the effective capacitance of the coil loop. For example, the dielectric material 303 may be air, rubber, plastic, or any other dielectric material. In one example, the dielectric material may be polytetrafluoroethylene (pTFE). Dielectric material 303 may be an insulating material surrounding the parallel conductive elements of first and second conductors 302-1, 302-2. Alternatively, first and second conductors 302-1, 302-2 may be twisted upon one another to form a twisted pair cable. As another example, dielectric material 303 may be a plastic material. First and second conductors 302-1, 302-2 may form a coaxial structure in which dielectric material 303 separates the first and second conductors. As one more example, the first and second conductors may be configured as planar strips.

In the example embodiment, the coupling electronics portion 203 is operably and communicatively coupled to RF system 30 to allow RF coil 202 to transmit and/or receive RF signals. In the illustrated embodiment, coupling electronics portion 203 includes a signal interface 358 configured to transmit and receive the RF signals. Signal interface 358 may transmit and receive the RF signals via a cable. The cable may be a 3-conductor triaxial cable having a center conductor, an inner shield, and an outer shield. The center conductor is connected to the RF signal and pre-amp control (RF), the inner shield is connected to ground (GND), and the outer shield is connected to the multi-control bias (diode decoupling control) (MC_BIAS). A 10V power connection may be carried on the same conductor as the RF signal.

In the example embodiment, as explained above with respect to FIG. 5A, coupling electronics portion 203 includes a decoupling circuit, impedance inverter circuit, and pre-amplifier. As illustrated in FIG. 5B, the decoupling circuit includes a decoupling diode 360. Decoupling diode 360 may be provided with voltage from MC_BIAS, for example, in order to turn decoupling diode 360 on. When on, decoupling diode 360 causes conductor 302-1 to short with conductor 302-2, thus causing the coil be off-resonance and hence decouple the coil during a transmit operation, for example.

In the example embodiment, the impedance inverter circuit includes a plurality of inductors, including first inductor 370a, second inductor 370b, and third inductor 370c; a plurality of capacitors, including first capacitor 372a, a second capacitor 372b, a third capacitor 372c, and a fourth capacitor 372d; and a diode 374. The impedance inverter circuit includes matching circuitry and an input balun. As shown, the input balun is a lattice balun that includes first inductor 370a, second inductor 370b, first capacitor 372a, and second capacitor 372b. In one example, diode 374 limits the direction of current flow to block RF receive signals from proceeding into decoupling bias branch (MC_BIAS).

In the example embodiment, the pre-amplifier 362 may be a low input impedance pre-amplifier that is optimized for high source impedance by the impedance matching circuitry. The pre-amplifier may have a low noise reflection coefficient, y, and a low noise resistance, Rn. In one example, the pre-amplifier may have a source reflection coefficient of y substantially equal to 0.0 and a normalized noise resistance of Rn substantially equal to 0.0 in addition to the low noise figure. However, y values substantially equal to or less than 0.1 and Rn values substantially equal to or less than 0.2 are also contemplated. With the pre-amplifier having the appropriate y and Rn values, the pre-amplifier provides a blocking impedance for RF coil 202 while also providing a large noise circle in the context of a Smith Chart. As such, current in RF coil 202 is minimized, the pre-amplifier is effectively noise matched with RF coil 202 output impedance. Having a large noise circle, the pre-amplifier yields an effective SNR over a variety of RF coil impedances while producing a high blocking impedance to RF coil 202.

In some examples, pre-amplifier 362 may include an impedance transformer that includes a capacitor and an inductor. The impedance transformer may be configured to alter the impedance of the pre-amplifier to effectively cancel out a reactance of the pre-amplifier, such as capacitance caused by a parasitic capacitance effect. Parasitic capacitance effects can be caused by, for example, a PCB layout of the pre-amplifier or by a gate of the pre-amplifier. Further, such reactance may often increase as the frequency increases. Advantageously, however, configuring the impedance transformer of the pre-amplifier to cancel, or at least minimize, reactance maintains a high impedance (i.e. a blocking impedance) to RF coil 202 and an effective SNR without having a substantial impact on the noise figure of the pre-amplifier. The lattice balun described above may be a non-limiting example of an impedance transformer.

In examples, the pre-amplifier described herein may be a low input pre-amplifier. For example, in some embodiments, a "relatively low" input impedance of the preamplifier is less than approximately 5 ohms at resonance frequency. The coil impedance of RF coil 202 may have any value, which may be dependent on coil loading, coil size, field strength, and/or the like. Examples of the coil impedance of RF coil 202 include, but are not limited to, between approximately 2 ohms and approximately 10 ohms at 1.5 T magnetic field strength. The impedance inverter circuitry is configured to transform the coil impedance of RF coil 202 into a relatively high source impedance. For example, in some embodiments, a "relatively high" source impedance is at least approximately 100 ohms and may be greater than 150 ohms.

The impedance transformer may also provide a blocking impedance to RF coil 202. Transformation of the coil impedance of RF coil 202 to a relative high source impedance may enable the impedance transformer to provide a higher blocking impedance to RF coil 202. Example values for such higher blocking impedances include a blocking impedance of at least 1300 ohms, and at least 1000 ohms.

FIG. 5C shows a cross-sectional view of an example coil loop 201. In the example embodiment, coil loop 201 includes first wire conductor 302-1 and second wire conductor 302-2 surrounded by and encapsulated in dielectric material 303. Each wire conductor may have a suitable cross-sectional shape, herein a circular cross-sectional shape. However, other cross-sectional shapes for the wire conductors are possible, such as elliptical, cylindrical, rectangular, triangular, or hexagonal. The wire conductors may be separated by a suitable distance, and the distance separating the conductors as well as the diameters of the wire conductors may be selected to achieve a desired capacitance. Further, each of first wire conductor 302-1 and second wire conductor 302-2 may be a multi-strand wire conductor, which has a plurality of strands 395, such as a seven conductor stranded wire (e.g., having seven strands), but solid conductors may also be used instead of a stranded wire. A stranded wire may provide more flexibility than solid conductors, at least in some examples.

As appreciated in describing FIG. 5B, the two parallel conductors including the coil loop of an RF coil may each be continuous conductors, or one or both of the conductors may be non-continuous, as illustrated in FIG. 5B. For example, both conductors shown in FIG. 5B may include cuts, resulting in each conductor having two segments. The resulting space between conductor segments may be filled with the dielectric material that encapsulates and surrounds the conductors. The two cuts may be positioned at different locations, e.g., one cut at 135° and the other cut at 225° (relative to where the coil loop interfaces with the coupling electronics). By including discontinuous conductors, the resonance frequency of the coil may be adjusted relative to a coil that includes continuous conductors. In an example, an RF coil that includes two continuous parallel conductors encapsulated and separated by a dielectric, the resonance frequency may be a smaller, first resonance frequency. If that RF coil instead includes one discontinuous conductor (e.g., where one of the conductors is cut and filled with the dielectric material) and one continuous conductor, with all other parameters (e.g., the conductor wire gauge, loop diameter, spacing between conductors, dielectric material) being the same, the resonance frequency of the RF coil may be a larger, second resonance frequency. In this way, parameters of the coil loop, including conductor wire gauge, loop diameter, spacing between conductors, dielectric material selection and/or thickness, and conductor segment number and lengths, may be adjusted to tune the RF coil to a desired resonance frequency.

FIG. 5D is a cross-sectional view of a wire conductor 302-5D used in coil loop 201 of RF coils 202. Different from coil loops 201 shown in FIG. 5B that include first conductor 302-1, second conductor 302-2, and two driven ends at each end of the conductors, coil loops 201 may include one single wire conductor 302-5D and one driven end 312 at each end of wire conductor 302-5D. When wire conductor 302-5D is used, driven end 312-1 is coupled with an end of wire conductor 302-5D and driven end 312-2 is coupled with the other end of wire conductor 302-5D. Coil loop 201 may form into one turn or a plurality of turns. The resistance of coil loop 201 increases approximately by number of turns, and the loop loss increases approximately by square root of the number of turns, while the body loss increases approximately by the number of turns. As a result, the SNR of coil loop 201 is increased approximately by the square root of the number of turns, such that multiple turns are used to increase the ratio of the body loss over the loop loss, compared with a single turn coil loop. Coil loop 201 forms into a shape of a circle, and may form into other shapes such as a polygon, oval, or irregular shapes. Coil loop 201 defines a conductive pathway along wire conductor 302-5D. Wire conductor 302-5D may be uninterrupted and continuous along an entire length of the coil loop. The coil loop may also include loops of varying gauge of stranded or solid conductor wire, or loops of varying diameters with varying lengths of conductors 302-5D. For example, conductor 302-5D may have no cuts or gaps (no segmented conductors) or one or more cuts or gaps (segmented conductors) at various locations along the conductive pathway. One or more capacitors may be placed at the cuts, gaps, or at the end of the coil loop before driven end 312-2. The capacitance of capacitors may be variable.

In the example embodiment, conductor 302-5D has a suitable cross-sectional shape, such as circular, elliptical, rectangular, triangular, or other shapes that enable conductor 302-5D functions as described herein. Insulating material 303 surrounds conductors 302-5D. Dielectric material 303 may be rubber, plastic, or any other dielectric material. conductor 302-5D includes one or a plurality of strands 395. For example, conductor 302-5D is a single-strand wire conductor. Alternatively, conductor 302-5D is a multi-strand wire conductor having a plurality of strands 395, where an individual strand 395 may be surrounded by insulating material or not surrounded by insulating material. Individual strands 395 may be twisted upon each other or may be parallel to each other, along the length of strand 395. In one example, wire conductor 302-5D includes 19 strands that are 36 AWG each for an overall thickness of 24 AWG, and the cross section of wire conductor 302-5D has a diameter of 0.025 inches (0.06 cm). A coil loop 201 including multi-strand conductors 302-5D has a higher penetration depth and a higher SNR than a coil loop 201 of the same diameter that includes a single-strand conductor. Therefore, the size of coil loop 201 may be reduced by including multi-strand wire conductors 302-5D for the same penetration depth, and consequently an increased number of RF coils 202 may be included in a coil array.

The RF coils 202 presented above with respect to FIG. 5A may be used in order to receive MR signals during an MR imaging session. As such, the RF coils of FIG. 5A are configured to be coupled to downstream components of MR system 10. RF coils 202 of FIG. 5A may be present in an array of RF coils having various configurations.

Figure 6A:
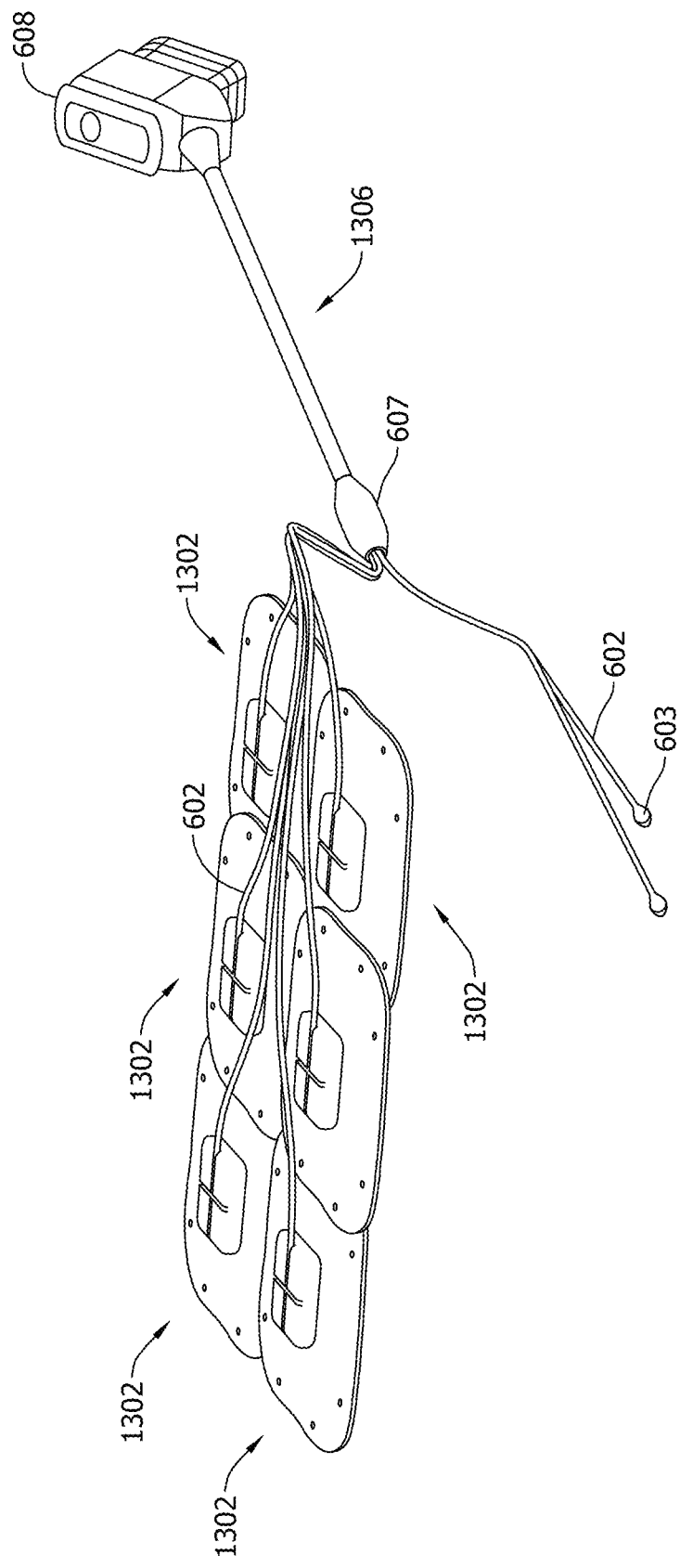
FIG. 6A is a perspective view of an example RF coil assembly.
Figure 6B:
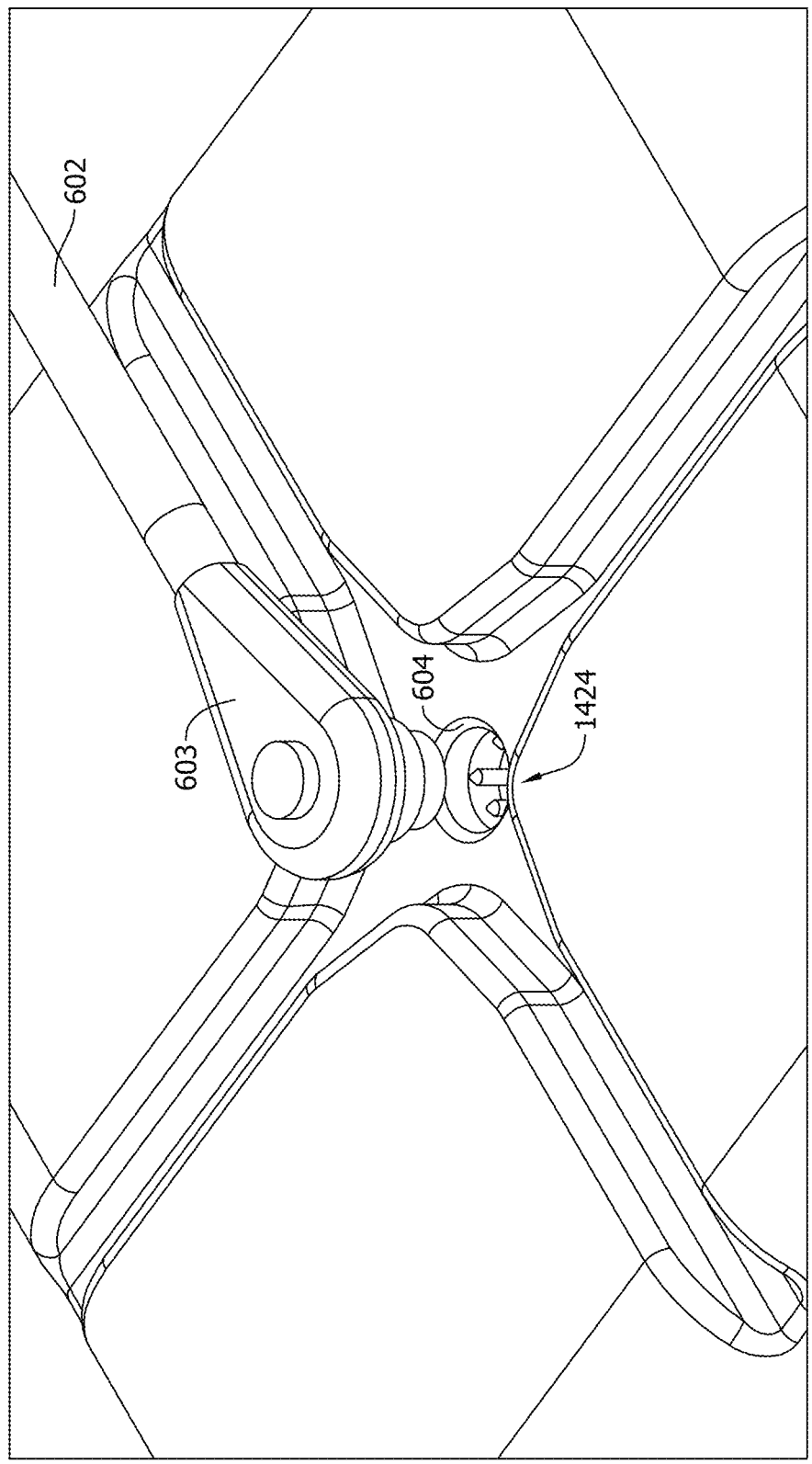
FIG. 6B illustrates a portion of the RF coil assembly shown in FIG. 6A with a wiring harness unplugged from a module.

FIGS. 6A and 6B shows example wiring harness 1306. In the example embodiment, wiring harness 1306 includes a plurality of module interfacing cables 602 extending from a module interfacing connector 603. Module interfacing cables 602 may be used to connect the RF coil assembly 1300 to other components of the MR system 10 such as the RF system 30 through a coil assembly interfacing connector 608. The module interfacing cable 602 may include a baluns 607 or contiguous/continuous distributed baluns (not shown).

In the example embodiment, coupling electronics portions 203 or part of coupling electronics portions 203 are assembled in electronics box 1414. Electronics box 1414 includes an outlet 604 configured to electrically couple with module interfacing connector 603, which is electrically coupled with coil assembly interfacing connector 608. Coil assembly interfacing connector 608 further couples to other components of MR system 10 such as RF system 30. For example, when RF coil assembly 1300 is in use, coil assembly interfacing connector 608 is plugged in a coil interface (not shown) or port, coupling RF coil assembly 1300 to the rest of the MR system 10, such as RF system 30.

In the example embodiment, RF coil assembly 1300 further includes a control circuitry. The control circuitry is the MC_BIAS for switching RF coils between receive and decoupled modes (see FIG. 5B). Elements of the control circuitry may be incorporated in coupling electronics portion 203, module interfacing connector 603, and/or coil assembly interfacing connector 608.

In the example embodiment, RF coil assembly 1300 is flexible without increased stress on coil loops 201 and other components of RF coil assembly 1300. As used herein, an RF coil assembly is flexible when the RF coil assembly may be flexed or bent to change the shape of the RF coil assembly. The RF coils 202 described above are configured to maintain the performance while the RF coils are flexed or bent.

In some embodiments, modules 1302 wirelessly communicate with coil assembly interfacing connector 608 or RF system 30. Module interfacing cables 602 are removed. Outlet 604 of module 1302 may include a wireless communication connector, such as a radio wave transmitter and receiver, configured to wirelessly communicate with coil assembly interfacing connector 608 or RF system 30. Signals are transmitted between modules 1302 and coil assembly interfacing connector 608 and further to RF system 30, or directly between modules 1302 and RF system 30.

In operation, to assembly an RF coil assembly 1300, modules 1302 are coupled with one another. Modules 1302 may be coupled with one another via coupler 1408. Electronics boxes 1414 of coupled modules 1302 may be positioned on the same side of RF coil assembly (see FIG. 6A). Alternatively, electronics boxes 1414 may face any direction. Module interfacing cables 602 are coupled with outlets 604 of modules 1302. Module interfacing cables 602 may be plugged into outlets 604. In some embodiments, wiring harness 1306 is coupled with modules 1302 by powering on outlet 604 to provide wireless communication. In other embodiments, wiring harness 1306 is eliminated and modules 1302 communicate wirelessly with RF system 30. During scanning, RF coil assembly 1300 is placed on the subject. Electronics boxes 1414 may face away from the subject, to increase patient comfort. Coil assembly interfacing connector 608 is plugged into a port of MR system 10.

As described above, in MR, signals are acquired by an RF coil. Therefore, an RF coil plays a major role in image quality, such as SNR or image distortion, of images acquired by the MR system. RF coils are desirable to be flexible such that RF coils conform to and are proximate to the anatomy of the subject. RF coil assemblies 1300 described herein accomplish this goal.

Figure 7B:
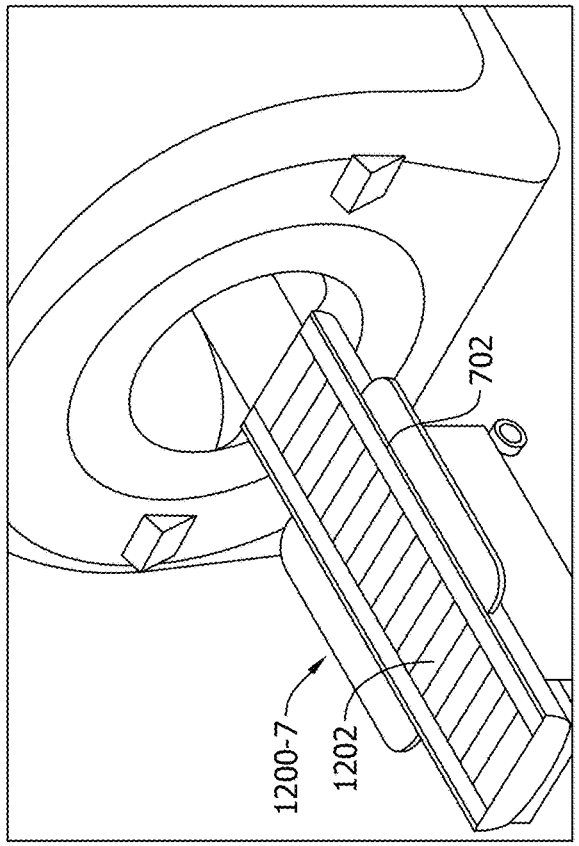
FIG. 7B shows the known coil assembly with the top cover removed.
Figure 7A:
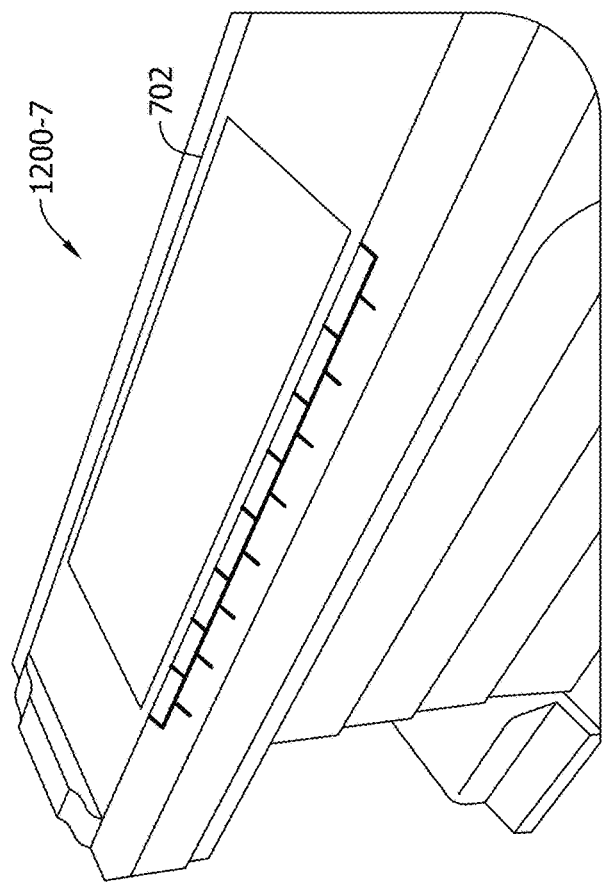
FIG. 7A shows another known modular coil assembly.
Figure 7C:
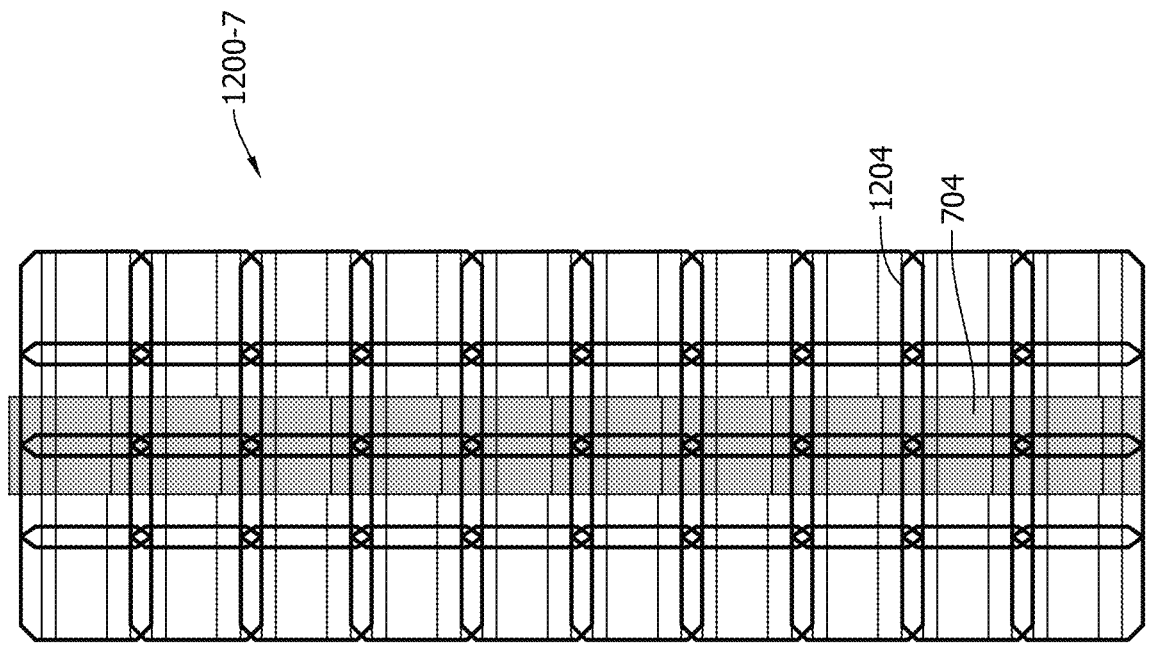
FIG. 7C shows the coil loops of the known coil assembly.
Figure 8A:
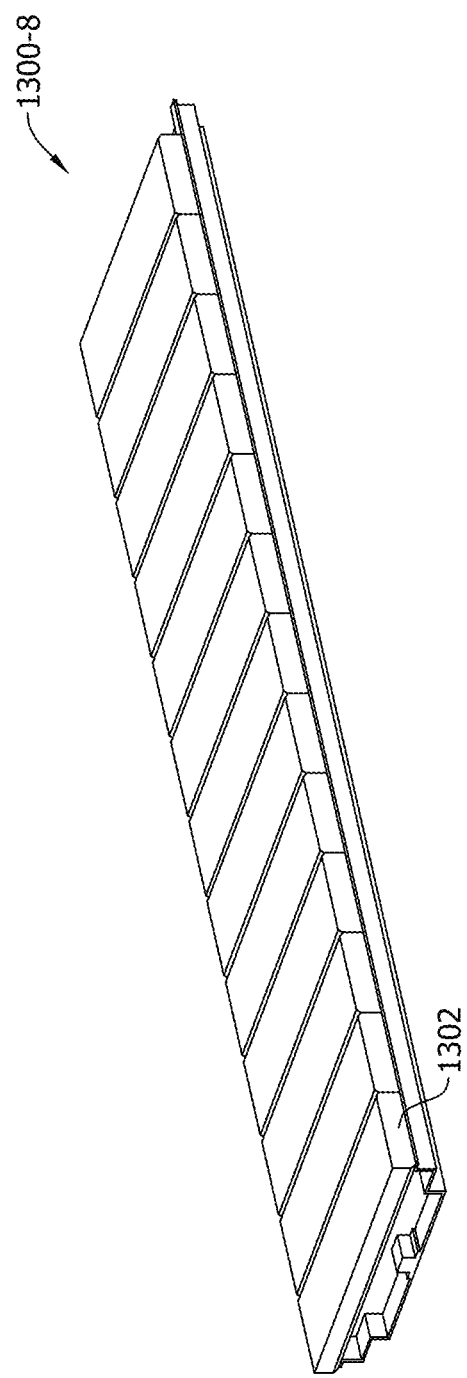
FIG. 8A shows one more example coil assembly.

FIGS. 7A-7C show another known modular RF coil assembly 1200-7. Like the other known RF coil assembly 1200-2, known RF coil assembly 1200-7 is constructed with rigid coil loops 1204 of copper strips. Coil loops 1204 are coupled with neighboring coil loops at a predefined configuration such that a coil loop 1204 is critically overlapped with its neighboring coil loops. To maintain the formation, RF coil assembly 1200-7 is embedded in a patient table 702 of the MR system (FIGS. 7A and 7B). Modules 1202 are connected to a common strip line 704 embedded in table 702.

FIGS. 8A-8D show more example embodiments of RF coil assembly 1300-8. In the example embodiments, module 1302 of RF coil assembly 1300 includes RF coils in arrays. RF coils may be RF coils 202 described above. In some embodiment, coil loops of RF coil assembly 1300 may be fabricated with metal strips. RF coils may be form in arrays. RF coil assembly 1300-8 may include a strip line 804 through modules 1302 and configured to transmit signals to and from modules 1302. Modules 1302 may be pluggable into strip line 804.

Compared to known RF coil assembly 1200-7, modules 1302 of RF coil assembly 1300 may have different dimensions and may include different numbers of RF coils therein. In known RF coil assembly 1200-7, each module 1202 has the same number of RF coils, such as 1×4 or 2×4 (see FIG. 7B). In contrast, modules 1302 of RF coil assembly 1300 have different dimensions. For example, module 1302-$s$ is smaller than module 1302-1 and may include a fewer number of RF coils. Module 1302-$s$ may include 1×4 RF coils while module 1302-1 may include 4×4 RF coils. Different sizes of modules 1302 may be included in constructing RF coil assembly 1300 such that different sizes of field of view FOV may be used to scan different areas of anatomies of subject 1304. For example, to scan a head 806, a desired FOV is the size of head 806 such as 20 cm. A small module 1302-$s$ may be placed at an end 808 of RF coil assembly 1300 (see FIGS. 8B-8D). Similarly, if images of feet 810 or legs 812 are to be acquired, small modules 1302-$s$ are placed at corresponding sections of RF coil assembly 1300 (see FIGS. 8C and 8D). If images of a large FOV of subject 1304 are desired, large modules 1302-1 are placed at corresponding part of subject 1304.

Compared to known RF coil assembly 1200-2, 1200-7, RF coil assembly 1300 is advantageous for being serviceable. For example, in known RF coil assembly 1200, modules 1202 need to be placed at a predefined configuration and coupling of modules 1202 are complicated, nonfunctioning of one module 1202 renders nonfunctioning of the entire RF coil assembly 1200. A clinician may not simply replace the nonfunctioning module with a spare module because of the strict predefined configuration and complicated coupling. Further, because known RF coil assembly 1200-7 is embedded in table 702, if a module 1302 does not function and needs to be repaired, a clinician could not simply replace the nonfunctioning module 1202 and return RF coil assembly 1200 to operation. A service is needed to take the table apart, remove the nonfunctioning module 1202, replace with a new module, and return RF coil assembly 1200 to functioning state.

In contrast, RF coil assembly 1300 is serviceable. a clinician may simply replace the nonfunctioning module with a spare module stored in the scanner room and return RF coil assembly to operation. Further, modules 1302 are individually controlled and connected with MR system 10. If a spare module 1302 is not available, the rest of RF coil assembly 1300 still functions, without interruption of operation.

When RF coil assembly 1300 includes RF coil 202 having coil loop 201 formed by wire conductor 302, because of the flexibility of wire conductor 302 and outer enclosure, modules 1302 are flexible and deformable and configured to deform into shapes congruent with the shapes of subject 1304 such that RF coils 202 are placed close to anatomies of interest, thereby increasing SNR of the signals received by RF coil assembly 1300 and efficiency of RF coil assembly 1300. Further, wire conductor 302, RF coil 202, and outer enclosure 1420 are lighter than traditional RF coil assembly. The weight of RF coil assemblies described herein is significantly reduced. For example, the known RF coil assembly 1200-2 may weigh 1 lb or more for one module, which may be unsuitable to be placed on a child, an elderly, or a sick subject. In contrast, RF coil assemblies described herein weighs approximately 0.5 g/cm$^2$, suitable to be placed on any subject, thereby increasing subject comfort.

Because modules 1302 in RF coil assembly 1300 may be manufactured using the same material, the material cost may be reduced. With modular RF coil assembly 1300, the number of different components in an RF coil assembly is greatly reduced. Therefore, the number of suppliers is reduced, increasing the quality of an RF coil assembly and reducing the repair cost. Further, because the process of building and tuning the RF coil assemblies becomes the same for the same modules, the manufacturing process is controlled and automated, and waste from manufacturing is controlled, thereby reducing cost of labor and overhead. In addition, because the modules are replaceable and serviceable in the field rather than incurring down time from waiting for replacement of the entire RF coil assembly in known RF coil assemblies, the repair cost as well as shipping costs are reduced.

Because modules 1302 of RF coil assembly 1300 may be arranged in any orientation, and overlapped or underlapped at any distance, RF coil assembly 1300 may be configured as an anterior RF coil assembly, a posterior RF coil assembly, a head RF coil assembly, a whole body assembly, a musculoskeletal (MSK) RF coil assembly, or any combination thereof. RF coil assembly 1300 may be configured as having two or more types of coils such as a head RF coil assembly and an anterior RF coil assembly by including two groups of modules 1302 in RF coil assembly 1300 with groups underlapped from one another. As a result, flexibility in constructing RF coil assembly 1300 is significantly increased.

RF coil assemblies described herein are also advantageous over a mere inclusion of multiple RF coil assemblies in MR system 10. MR system 10 has a limited number of ports for RF coils to be plugged in. MR system 10 typically has four ports. Therefore, the number of RF coil assemblies are conventional limited to four. In MR systems, because of the interactions between RF and magnetic field, care is needed in placement of cables of RF coil assemblies to avoid cross talk or signal loss. Cables need to long for the RF coil assemblies to be plugged in the ports. The long cables are also cumbersome in set-up with a subject because the long cables should be placed away from the subject to provide comfort. In contrast, RF coil assemblies described herein need one port for one RF coil assembly, increasing the flexibility of MR system 10 and the number of RF coil assemblies in MR system 10. Because modules 1302 are coupled to wiring harness 1306, problems associated with multiple long cables are obviated.

RF coil assemblies described herein are also advantageous in providing flexibility in system setup. Modules to be included in an RF coil assembly may be customized to fit imaging needs. For example, modules of relatively small dimensions may be used to image a small FOV, such as the head. Modules of relatively big dimensions may be used to image a large FOV, such as the spine. Therefore, when imaging a small FOV, a large RF coil assembly is not placed on the subject, thereby increasing patient comfort, image quality, and SNR because small coil loops are closer to anatomies of interest than large coil loops. RF coil assemblies provides the capabilities of imaging a large FOV without the need of using a separate RF coil assembly. Instead, a large module or large modules are included in one RF coil assembly. Further, the changes may be performed by a clinician because a module may be plugged in or removed from an RF coil assembly.

FIG. 9 is a flow chart of an example method 900 of assembling an RF coil assembly. The RF coil assembly may be RF coil assemblies 1300 described above. Method 900 includes providing 902 a first module and a second module. Modules may be modules 1302 described above. Method 900 further includes coupling 904 the first module with the second module. Method 900 also includes coupling 906 the modules with the RF system of the MR system. Coupled modules 1302 may be coupled to RF system 30 via a wiring harness 1306. In some embodiment, coupled modules 1302 is coupled with common strip line 804, which is configured to couple with RF system 30. In other embodiments, coupled modules 1302 are coupled with RF system 30 through wireless communication.

At least one technical effect of the systems and methods described herein includes (a) modular RF coil assemblies; (b) a wiring harness for coupling modules; (c) pluggable connections between modules and the wiring harness; (d) flexibility in construction of an RF coil assembly; (e) a serviceable RF coil assembly, and (d) a simplified assembling process.

Example embodiments of assemblies, systems, and methods of RF coil assemblies are described above in detail. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A radio frequency (RF) coil assembly for a magnetic resonance (MR) system, comprising:
    one or more modules, a module of the one or more modules comprising:
        one or more RF coils, each RF coil comprising:
            a coil loop that comprises a wire conductor, the wire conductor formed into the coil loop; and
            a coupling electronics portion coupled with the coil loop; and
        an outer enclosure housing the one or more RF coils and separating one of the one or more modules from another one of the one or more modules; and
        an outlet coupled with coupling electronics portions of the one or more RF coils; and
    a wiring harness comprising a plurality of module interfacing cables and a coil assembly interfacing connector, the plurality of module interfacing cables bundled and extending from the coil assembly interfacing connector, the plurality of module interfacing cables comprising one or more baluns, one of the plurality of module interfacing cables configured to be coupled with an outlet of the one of the one or more modules, another one of the plurality of module interfacing cables configured to be coupled with an outlet of another one of the one or more modules.

2. The RF coil assembly of claim 1, wherein the one of the plurality of module interfacing cables of the wiring harness is pluggable in the outlet of the one of the one or more modules.

3. The RF coil assembly of claim 1, wherein one of the one or more modules overlaps with another one of the one or more modules at an arbitrary orientation.

4. The RF coil assembly of claim 1, wherein the wiring harness is configured to be electrically coupled to a port of the MR system.

5. The RF coil assembly of claim 1, wherein a first module of the one or more modules overlaps with a second module of the one or more modules and underlaps with a third module of the one or more modules.

6. The RF coil assembly of claim 1, wherein the module further comprises:
    a coupler configured to couple with a coupler of another module.

7. The RF coil assembly of claim 6, wherein a first module is critically overlapped with a second module when a coupler of the first module is aligned with a coupler of the second module.

8. The RF coil assembly of claim 1, wherein the module further comprises:
    an electronics box sized to house coupling electronics portions of the one or more RF coils and the outlet.

9. The RF coil assembly of claim 8,
    wherein the electronics box is positioned at an exterior of the outer enclosure.

10. A radio frequency (RF) coil assembly for a magnetic resonance (MR) system, comprising:
    a first module comprising:
        a first number of RF coils, each RF coil comprising a coil loop; and
        a first outer enclosure housing coil loops of the first number of RF coils;
    a second module comprising:
        a second number of RF coils, the second number being different from the first number; and
        a second outer enclosure housing coil loops of the second number of RF coils,
        wherein the first module and the second module are configured to be installed on a table of the MR system; and
    a strip line configured to be installed in the table of the MR system, the strip line extending through the first module and the second module and configured to individually couple with the first module and the second module.

11. The RF coil assembly of claim 10, wherein the coil loop further comprises a wire conductor, the wire conductor formed into the coil loop, and the RF coil further comprises:
    a coupling electronics portion coupled with the coil loop.

12. The RF coil assembly of claim 11, wherein the first outer enclosure and the second outer enclosure are configured to deform into shapes congruent with a shape of a subject of the MR system.

13. The RF coil assembly of claim 10, wherein at least one of the first module or the second module is pluggable into the strip line.

14. A module of a radio frequency (RF) coil assembly for a magnetic resonance (MR) system, comprising:
    one or more RF coils, each RF coil comprising:
        a coil loop that comprises a wire conductor, the wire conductor formed into the coil loop; and
        a coupling electronics portion coupled with the coil loop;
    an outer enclosure housing the one or more RF coils and separating the module from another module; and
    an outlet extending through the outer enclosure and coupled with coupling electronics portions of the one or more RF coils, the outlet being exposed and configured to individually establish wired communication between the module and the MR system via a wiring harness, wherein the wiring harness includes a plurality of module interfacing cables and a coil assembly interfacing connector, the plurality of module interfacing cables bundled and extending from the coil assembly interfacing connector, one of the plurality of module interfacing cables configured to be coupled with the outlet, another one of the plurality of module interfacing cables configured to be coupled with an outlet of another module.

15. The module of claim 14, wherein the outlet is complementary to the one of the plurality of module interfacing cables of the wiring harness, thereby being pluggable in coupling with the one of the plurality of module interfacing cables of the wiring harness.

16. The module of claim 14, wherein the module further comprises:
    a coupler configured to couple with a coupler of another module.

17. The module of claim 16, wherein the module is critically overlapped with another module when the coupler of the module is aligned with the coupler of another module.

18. The module of claim 14, wherein the module further comprises:
- an electronics box sized to house coupling electronics portions of the one or more RF coils and the outlet.

19. The module of claim 18, wherein the module further comprises:
- an outer enclosure housing coil loops of the one or more RF coils,
- wherein the electronics box is positioned at an exterior of the outer enclosure.

* * * * *